United States Patent
Li et al.

(10) Patent No.: US 12,097,254 B2
(45) Date of Patent: Sep. 24, 2024

(54) RABIES COMPOSITION COMPRISING PIKA ADJUVANT

(71) Applicant: Yisheng Biopharma (Singapore) PTE LTD, Singapore (SG)

(72) Inventors: Lietao Li, Singapore (SG); Yi Zhang, Beijing (CN); Fang Liu, Beijing (CN)

(73) Assignee: Yisheng Biopharma (Singapore) PTE LTD, Singapore (SG)

( * ) Notice: Subject to any disclaimer, the term of this patent is extended or adjusted under 35 U.S.C. 154(b) by 335 days.

(21) Appl. No.: 17/211,632

(22) Filed: Mar. 24, 2021

(65) Prior Publication Data
US 2022/0040289 A1 Feb. 10, 2022

Related U.S. Application Data

(63) Continuation of application No. 15/534,450, filed as application No. PCT/SG2014/000614 on Dec. 23, 2014, now abandoned.

(51) Int. Cl.
| | |
|---|---|
| *A61K 39/205* | (2006.01) |
| *A61K 9/19* | (2006.01) |
| *A61K 39/12* | (2006.01) |
| *C12N 7/00* | (2006.01) |
| *A61K 39/00* | (2006.01) |

(52) U.S. Cl.
CPC .............. *A61K 39/205* (2013.01); *A61K 9/19* (2013.01); *A61K 39/12* (2013.01); *C12N 7/00* (2013.01); *A61K 2039/5252* (2013.01); *A61K 2039/545* (2013.01); *A61K 2039/55* (2013.01); *A61K 2039/552* (2013.01); *A61K 2039/55511* (2013.01); *A61K 2039/55516* (2013.01); *A61K 2039/55561* (2013.01); *C12N 2760/20134* (2013.01)

(58) Field of Classification Search
None
See application file for complete search history.

(56) References Cited

U.S. PATENT DOCUMENTS 3,666,646 A    5/1972 Lampson et al.
3,692,899 A    9/1972 Levy
(Continued)

FOREIGN PATENT DOCUMENTS

CN    1095951    12/1994
CN    93105862.7    9/2000
(Continued)

OTHER PUBLICATIONS

US 6,008,200 A, 12/1999, Krieg et al. (withdrawn)
(Continued)

*Primary Examiner* — M Franco G Salvoza
(74) *Attorney, Agent, or Firm* — Finnegan, Henderson, Farabow, Garrett & Dunner LLP

(57) ABSTRACT

The present disclosure provides a rabies composition comprising IPRV and PIKA adjuvant, and the pharmaceutical use thereof. The present disclosure also discloses a method for prophylaxis or therapeutic treatment of rabies virus infection, the method comprises a step of administering the rabies vaccine composition to a host. The rabies composition is more stable and safe, and is able to induce earlier and higher titers of neutralizing antibody.

29 Claims, 2 Drawing Sheets

| | IPRV/dose (IU) | IPRV/dose (ug) | IPRV dose IU(kg) | PIKA dose (ug/kg) | IPRV HED* (x60kg) | PIKA HED* (x60kg) |
|---|---|---|---|---|---|---|
| Ex.1 and Ex.2 | | | Body weight (kg) = 0.02 | | Conversion factor = 12.3 | |
| Humoral immune response | 0.1 | 10 | 5.000 | 500.00 | 24.39 | 2,439 |
| Viral challenge test | 0.1 | 50 | 5.000 | 2,500.00 | 24.39 | 12,195 |
| IL-2 Induction & Macrophage activation | 0.1 | 10 | 5.000 | 500.00 | 24.39 | 2,439 |
| IFN-gamma production | 0.2 | 50 | 10.000 | 2,500.00 | 48.78 | 12,195 |
| Ex.5 Hamster Protection Test | | | Body weight (kg) = 0.15 | | Conversion factor = 7.4 | |
| IPRV (1-1-1-1-1) | 0.4 | 0.4 | 2.667 | | 21.62 | |
| Full dose (2-2-1) | 0.2 | 100 | 1.333 | 666.67 | 10.81 | 5,405 |
| Full dose (1-1-1-1-1) | 0.2 | 100 | 1.333 | 666.67 | 10.81 | 5,405 |
| Ex.6 Mice Protection Test | | | Body weight (kg) = 0.02 | | Conversion factor = 12.3 | |
| PIKA IPRV | 0.09 | 60 | 4.500 | 3,000.00 | 21.95 | 14,634 |

*HED: Human equivalent dose

(56) References Cited

U.S. PATENT DOCUMENTS

| | | | |
|---|---|---|---|
| 3,906,092 | A | 9/1975 | Hilleman et al. |
| 3,952,097 | A | 4/1976 | Levy |
| 4,024,241 | A | 5/1977 | Levy |
| 4,082,735 | A | 4/1978 | Jones et al. |
| 4,082,736 | A | 4/1978 | Jones et al. |
| 4,094,971 | A | 6/1978 | Chedid et al. |
| 4,101,536 | A | 7/1978 | Yamamura et al. |
| 4,124,702 | A | 11/1978 | Lampson et al. |
| 4,140,761 | A | 2/1979 | Gerin et al. |
| 4,153,684 | A | 5/1979 | Audibert et al. |
| 4,164,565 | A | 8/1979 | Prince et al. |
| 4,185,089 | A | 1/1980 | Derrien et al. |
| 4,186,194 | A | 1/1980 | Adam et al. |
| 4,235,771 | A | 11/1980 | Adam et al. |
| 4,314,998 | A | 2/1982 | Yamamura et al. |
| 4,323,559 | A | 4/1982 | Audibert et al. |
| 4,327,085 | A | 4/1982 | Audibert et al. |
| 4,349,538 | A | 9/1982 | Levy |
| 4,369,178 | A | 1/1983 | Yamamura et al. |
| 4,389,395 | A | 6/1983 | Lerner et al. |
| 4,954,298 | A | 9/1990 | Yamamoto et al. |
| 6,468,558 | B2 | 10/2002 | Wong |
| 2006/0275776 | A1 | 12/2006 | Banzhoff et al. |
| 2007/0166239 | A1 | 7/2007 | Lin et al. |
| 2007/0166800 | A1 | 7/2007 | Lin et al. |
| 2011/0081380 | A1 | 4/2011 | Francon et al. |
| 2013/0115244 | A1 | 5/2013 | Lin et al. |
| 2017/0340727 | A1 | 11/2017 | Lin et al. |

FOREIGN PATENT DOCUMENTS

| | | |
|---|---|---|
| CN | 102949716 A | 3/2013 |
| EP | 0025766 A3 | 9/1980 |
| EP | 1593392 | 9/2005 |
| FR | 2476488 | 8/1981 |
| JP | 57002220 | 1/1982 |
| JP | 01093540 | 4/1989 |
| JP | 1186818 | 7/1989 |
| WO | WO2005014038 | 2/2005 |
| WO | WO2006131023 | 12/2006 |

OTHER PUBLICATIONS

English translation of Zhang et al. (CN102949716A) (Year: 2013).*
Bertoletti (2012) PIKA dose response to determine effective concentration for monocyte-derived DC activation Singapore Institute for Clinical Sciences Biomedical Sciences Institutes. pp. 77-79.
Champney et al. (1979) Modified polyriboinosinic-polyribocytidylic acid complex: sustained interferonemia and its physiological associates in humans Infect Immun. September; 25(3): 831-837.
De Clercq et al. (1979) "Degradation of Poly(inosinic acid)-poly(cytidylic acid) [(On-(Cn)] by Human Plasma European" Journal of Biochemistry vol. 93 Issue 1 pp. 165-172.
Ellouz (1974) "Minimal structural requirements for adjuvant activity of bacterial peptidoglycan derivatives" Biochemical and Biophysical Research Communications. vol. 59 No. 4 pp. 1317-1325.
Finke et al., (2012) "Assessment of inactivated human rabies vaccines: Biochemical characterization and genetic identification of virus strains", Vaccine, 30(24):3603-3609.
Gai et al. (2011) PIKA Provides an Adjuvant Effect to Induce Strong Mucosal and Systemic Humoral Immunity Against SARS-CoV p. 81-94.
Gatmaitan et al. (1980) "Modified Polyriboinosiniic-Polyribocytidylic Acid Complex: Induction of Serum Interferon Fever and Hypotension in Rabbits" Antimicrobial agents and chemotherapy, p. 49-54.
Gupta et al (1993) Adjuvants—a balance between toxicity and adjuvanticity. Vaccine. vol. 11 pp. 293-306.
Gupta et al (1995) "Adjuvants for human vaccines—current status problems and future prospects" Vaccine. 1995 vol. 13 No. 14 pp. 1263-1278.
Houston et al (1976) "Modified Polyriboinosinic-Polyribocytidylic Acid an Immunological Adjuvant" Infection and Immunity American Society for Microbiology vol. 14(1) p. 318-319.
HU (1983) "Tianjin Poly I:C Laboratory Research and Clinical Application" Fujian Medical Journal. vol. 12 No. 6 pp. 31-34. (With English Abstract).
Jackson et al (2003) "Management of rabies in humans" Clin Infect Dis 36:60-63.
Kanzler et al. (2007) "Therapeutic targeting of innate immunity with toll-like receptor agonists and antagonists" Nature Medicine. 2007 vol. 13 No. 5 pp. 552-559.
Kende et al.(1987) "Enhanced Therapeutic Efficacy of Poly(ICLC) and Ribavirin Combinations against Rift Valley Fever Virus Infection in Mice" Antimicrobial Agents and Chemotherapy American Society for Microbiology vol. 31(7) p. 986-990.
Kenney et al. (2002) "Meeting report 2nd meeting on novel adjuvants currently in/close to human clinical testing World Health Organization—Organization Mondiale de la Sante Fondation Merieux Annecy France Jun. 5-7, 200" Vaccine vol. 20 pp. 2155-2163.
Lake et al. (1994) "Involvement of protein kinase C in macrophages activation by poly (C)" American Journal of Physiology vol. 266(1) pp. 134-142.
Levy et al (1980) "Immune Modulating Effects Of Poly ICLC" Annals Academy Science p. 33-41.
Levy et al. (1981) "Interferon induction in primates by stabilized polyriboinosinic acid-polyribocytidylic acid: effect of component size" Infect Immun. Nov. 1981; 34(2): 416-421.
Lin et al (1993) "A new immunostimulatory complex (PICKCa) in experimental rabies: antiviral and adjuvant effects" vol. 131 p. 307-319.
Lin et al. (1998) "Experimental Study of Rabies Vaccine Plus Pika Adjuvant" Chinese Journal of Biologicals 11(3):4 pages Translated by Schreiber Translations Inc.
Machida et al. (1976) "Relationship between the molecular size of poly 1-poly C and its biological activity" Jpn J Microbiol. Apr; 20(2)-76.
Morahan et al. (1972) "Antiviral activity and side effects of polyriboinosinic-cytidylic acid complexes as affected by molecular size" Nat. Acad. Sci. USA April vol. 69 No. 4 842-846.
Norlund et al. (1970) Inhibition of biologic activity of Poly I: Poly C by human plasma (34492). Proc Soc Exp Biol Med. vol. 133 pp. 439-444.
Phillips et al. (1971) Systemic toxicity of polyinosinic acid: polycytidylic acid in rodents and dogs. Toxicology and Applied Pharmacology. pp. 220-230.
Putra et al (2013) Response to a rabies epidemic Bali Indonesia Emerging infectious diseases 19(4) 648.
Sela et al (1969). "Antigenicity: some molecular aspects" Science 1365-1374.
Shantavasinkul et al (210) Failure of rabies postexposure prophylaxis in patients presenting with unusual manifestations. CHI—Infectious Diseases 50(1) 77-79.
Shu et al. (1989) Biological function and application of Poly I:C the First Affiliated Hospital of Xian Medical College. Shanxi Journal of Medicine, 40-42.
Smorodintsev et al. (1978) "Comparative study of the toxicity of poly G-poly C and poly 1-poly Cin different objects" Vopr Virusol. pp. 201-206. (English Abstract Only).
Stern et al. (1970) A nuclease from animal serum which hydrolyzes double-stranded RNA. Biochemical and Biophysical Research Communications vol. 41 No. 3 pp. 608-614.
Stringfellow et al. (1980) "Interferon induction by and toxicity of polyriboinosinic acid [poly (rI)].polyribocytidylic acid [poly (rC)] mismatched analog poly (rI).poly[r(C12Uracil)n] and poly(rI).poly(rC) L-lysine complexed with carboxynnethylcellulose" Antinnicrob Agents Chemother; 17(6): 988-992.
Sudarshan et al. (2007). Assessing the burden of human rabies in India: results of a national multi-certer epidemiological survey. Int J Infect Dis 11:29-35.
Tso et al. (1976) "An Integrated and Comparative Study of the Antiviral Effects and Other Biological Properties of the Polyinosinic Acid-Polycytidylic Acid and Its Mismatched Analogues" Molecular Pharmacology vol. 12 299-312.
Wunner et al. (1988) "The molecular biology of rabies viruses" Review of Infectious Diseases p. 771-784.

(56) References Cited

OTHER PUBLICATIONS

World Health Organization (2007). Rabies vaccines WHO position paper.
World Health Organization (2014). Rabies Fact Sheet N° 99.
World Health Organization (2010). Current strategies for human rabies pre and post-exposure prophylaxis.
Wilde et al (1996) Failure of postexposure treatment of rabies in children. Clin Infect Dis Feb;22(2):228-32.
Wright et al. (1985) The adjuvant effects mycoviral dsRNA and polyinosinic:polycytidylic acid on the murine immune response. Biochemical and Biophysical Research Communications vol. 131 No. 2 pp. 949-955.
Xue et al. (2011) "HPLC determination of kanamycin sulfate in PIKA rabies for human use and PIKA adjuvant" Chin Pharm Annal. p. 1911-1993. (English Abstract Only).
Zong et al. (1993) "Study on Determining the Molecular Weight of PICKCa and Pl. PC with the Method of Polyacrylamide Gel Electrophoresis (PAGE)" Chinese Journal of Pharmaceutical Analysis 13:5219-222.

* cited by examiner

Figure 1

| | IPRV/dose(IU) | IPRV/dose(ug) | IPRV dose IU(kg) | PIKA dose (ug/kg) | IPRV HED* (x60kg) | PIKA HED* (x60kg) |
|---|---|---|---|---|---|---|
| Ex.1 and Ex.2 | | | Body weight (kg) = 0.02 | | Conversion factor = 12.3 | |
| Humoral immune response | 0.1 | 10 | 5.000 | 500.00 | 24.39 | 2,439 |
| Viral challenge test | 0.1 | 50 | 5.000 | 2,500.00 | 24.39 | 12,195 |
| IL-2 Induction & Macrophage activation | 0.1 | 10 | 5.000 | 500.00 | 24.39 | 2,439 |
| IFN-gamma production | 0.2 | 50 | 10.000 | 2,500.00 | 48.78 | 12,195 |
| Ex.5 Hamster Protection Test | | | Body weight (kg) = 0.15 | | Conversion factor = 7.4 | |
| IPRV (1-1-1-1-1) | 0.4 | 0.4 | 2.667 | | 21.62 | |
| Full dose (2-2-1) | 0.2 | 100 | 1.333 | 666.67 | 10.81 | 5,405 |
| Full dose (1-1-1-1-1) | 0.2 | 100 | 1.333 | 666.67 | 10.81 | 5,405 |
| Ex.6 Mice Protection Test | | | Body weight (kg) = 0.02 | | Conversion factor = 12.3 | |
| PIKA IPRV | 0.09 | 60 | 4.500 | 3,000.00 | 21.95 | 14,634 |
| *HED: Human equivalent dose | | | | | | |

Figure 2

CTN-IV → Inoculating ← Virus Culture Medium (pH7.35~7.45)

Vero Cell

Perfusing ← Virus Culture Medium (pH7.35~7.45)

Harvesting

Ultrafiltration & Concentration

Inactivating ← 1/4000 β-Propiolactone

Purifying ← PBS Buffer + HSA ph 7.6

Inactivated Purified Virus Antigen

RABIES COMPOSITION COMPRISING PIKA ADJUVANT

CROSS-REFERENCE TO RELATED APPLICATIONS

This application is a continuation of application Ser. No. 15/534,450, filed on Jun. 8, 2017, which is a United States national stage entry under 35 U.S.C. § 371 of International Application No. PCT/SG2014/000614, filed on Dec. 23, 2024.

FIELD OF INVENTION

The invention relates to immunological field, more particularly relates to a rabies composition for prophylactic or/and therapeutic treatment of rabies caused by rabies virus infection, the method and use thereof, and more particularly to a rabies vaccine composition for the prophylactic or/and therapeutic treatment of rabies caused by rabies virus infection with an accelerated schedule.

BACKGROUND OF INVENTION

Rabies virus is an enveloped virus with single strand RNA gene encoding five structural proteins. Rabies is a zoonosis that is transmitted from animal to human through contamination which carries saliva-borne virus, or through intact mucous membrane. The mortality rate is almost 100% after the onset of clinical symptoms, and it remains one of the most lethal infectious diseases known.

In more developed region, rabies infections through canine species are rare due to mandatory pet vaccinations, such as in the United States, the few human rabies cases are caused by rabid bats. In developing countries, human rabies transmitted by rabid dogs is more prevalent, causing 25,000-30,000 deaths each year in Indian alone. Stray dogs or puppies without vaccination are potential carriers and they cohabitate with victims such as children in villages. Programs to vaccinate stray dogs have generally failed in these regions. According to WHO report, there are more than 60,000 people die from rabies worldwide annually. The most prevalent region is Asia and Africa. Most recent rabies outbreak in Bali Indonesia threatens more than 130 lives.

To date, there is no effective treatment for rabies once infected. Treatment such as antiviral drug, steroid, immunomodulator and immunoglobulin infusion has generally been ineffective. Fortunately, rabies infection can be prevented by vaccination upon exposure to potential rabid animals with immediate local wound treatment and proper post-exposure prophylaxis (PEP). In more severe cases, co-administration of rabies immunoglobulin (RIG) may be needed. People with high occupational risk of animal bite are also recommended to take prophylaxis against rabies virus. Rabies antibody titers equal to or more than 0.5 international units (IU), determined by rapid fluorescent focus inhibition test (RFFIT) against a WHO reference serum, are considered protective in mammalian species. The details of test is described in: Laboratory Techniques in Rabies, Edited by F X Meslin, M M Kaplan H Koprowski, 4th Edition, ISBN 92 4 1544 1.

Commercial available rabies vaccines are based on fixed strains of rabies viruses, such as the pitman Moore (PM) strain, the Kissling strain of Challenge Virus Standard (CVS), or the Flury low egg passage (LEP) or high-egg-passage (HEP), fixed Evelyn Rokitniki Abelseth (ERA) strain of Street-Alabama-Dufferin (SAD) virus and different SAD variants. These viral strains are adapted into four major culture systems that are approved by WHO, including human diploid cell, chick or duck embryo, hamster kidney cell and vero cell line.

Adjuvants are generally compounds, that when administered with an antigen (either mixed with, or given prior to the administration of the antigen) enhances or modifies the immune response to that particular antigen. Aluminium was routinely added into rabies vaccine as an adjuvant to enhance the potency of the inactivated vaccine. However, aluminium has been found to delay antibody production and ineffective to provide better protection in post exposure test. Therefore, searches for suitable adjuvant for rabies vaccine are still ongoing.

Moreover, inactivated vaccine is unstable during the purification, freeze drying and storage. Chemical and/or biological stabilizing agents are therefore added to the vaccine solution. Examples of chemical stabilizing agents hitherto known are human albumin, gelatin hydrolyzate, sugar alcohols, amino acids and other non-toxic substances. Prince et al, U.S. Pat. No. 4,164,565 discloses the use of albumin as a stabilizer in vaccines. A typical rabies vaccine composition would thus comprise an antigen of the inactivated rabies virus cultured in suitable cell line, with or without adjuvant, and stabilized with albumin and other stabilizing agents or excipients.

For prophylactic purposes, the vaccines are usually given 3 times to generate about 3 to 4 years of immunity. Upon exposure to rabies virus, the vaccines are usually given four times at days 0, 3, 7 and 14, or five times with Essen schedule involving 5 injections at days 0, 3, 7, 14, and 28.

Post-exposure rabies vaccines are routinely administered to prevent the fatal disease after exposure to suspected animal carriers. Although millions of people receive PEP each year after being exposed to suspected rabid animals, there are still reports of death related to rabies after receiving PEP, or even with co-administration of immunoglobulin.

A study analysis of 1120 human rabies cases in China Guangxi shows that 27.2% of death was caused by vaccination failure; amongst which 78.2% death cases happen before the $5^{th}$ injection. These failures may be associated with delayed production of rabies virus neutralising antibodies (RVNA) by the rabies vaccine, lack of T cell mediated immunity response, lack of immune response due to individual variations, or deviations from WHO post-exposure treatment guidelines such as no injection of immunoglobulin.

Studies have shown that animals and humans could produce rabies virus neutralising antibody upon infection or in response to vaccination. Early animal studies have shown that vaccine induced IgM and IgG play important role in protecting the immunised animal from viral challenge. Thus, an early production of higher titers of neutralising antibody is vital in protecting patients who has potential exposure to virus.

On the other hand, there are studies testing and recommending new vaccination regimens that could improve vaccination efficacy, reduce clinical complexity (i.e. less injections or shorter clinical duration) and cost. European Patent No. 1 593 392 provides a method of pre- and post-immunization rabies vaccine with a reduced dose.

In this disclosure, we disclose a more potent rabies vaccine which is able to induce earlier and higher titers of rabies virus neutralizing antibody. The specific formulation described herein comprising inactivated purified rabies antigen, PIKA adjuvant and human serum albumin mixed in a buffer solution with or without other excipients is safe and stable for human use with long shelf-life. We further disclose a method of administering the composition with a novel vaccination regimen which requires lesser clinical visits and shorter immunization duration.

LITERATURE

The following references may be of interest:

Wunner, W. H., Larson, J. K., Dietzschold, B., & Smith, C. L. (1988). The molecular biology of rabies viruses. Review of Infectious Diseases, 10 (Supplement 4), S771-S784

Sudarshan M K, Madhusudana S N, Mahendra B J, Rao N S, Ashwath Narayana D H, et al. (2007). Assessing the burden of human rabies in India: results of a national multi-certer epidemiological survey. Int J Infect Dis 11:29-35.

Jackson A C, Warrell M J, Pupprecht C E, Ertl H C, Dietzschold B, et al. (2003). Management of rabies in humans. Clin Infect Dis 36:60-63.

World Health Organization (2014). Rabies Fact Sheet N° 99. Retrieved from: http://www.who.int/mediacentre/factsheets/fs099/en/

Putra, A. A. G., Hampson, K., Girardi, J., Hiby, E., Knobel, D., Mardiana, W., & Scott-Orr, H (2013). Response to a rabies epidemic, Bali, Indonesia, 2008-2011. Emerging infectious diseases, 19(4), 648.

World Health Organization (2010). Current strategies for human rabies pre and post-exposure prophylaxis. Retrieved from http://www.who.int/rabies/human/WHO strategy_prepost_exposure/en/

U.S. Pat. No. 4,164,565

Wang, S. et al (2010). A new PIKA adjuvant rabies vaccine. Journal of Applied preventive medicine 16(1), 1-4.

Deshmukh D G, Damle A S, Bajaj J K, Bhakre J B, Patil N S. Fatal rabies despite post-exposure prophylaxis. Indian J Med Microbiol. 2011 April-June; 29(2):178-80

Shantavasinkul, P., Tantawichien, T., Wacharapluesadee, S., Jeamanukoolkit, A., Udomchaisakul, P., Chattranukulchai, P., & Hemachudha, T. (2010). Failure of rabies postexposure prophylaxis in patients presenting with unusual manifestations. Clinical Infectious Diseases, 50(1), 77-79

Wilde H, Sirikawin S, Sabcharoen A, Kingnate D, Tantawichien T, Harischandra P A, Chaiyabutr N, de Silva D G, Fernando L, Liyanage J B, Sitprija V. Failure of postexposure treatment of rabies in children. Clin Infect Dis. 1996 February; 22(2):228-32

European Patent No. 1 593 392

Bertoletti, A, (2012) PIKA dose response to determine effective concentration for monocyte-derived DC activation. Singapore Institute for Clinical Sciences, Biomedical Sciences Institutes.

World Health Organization (2007). Rabies vaccines WHO position paper (1st ed.). Retrieved from http://www.who.int/immunization/sage/SAGEmeetingRabies_PP_Draft_oct12.pdf

SUMMARY OF THE INVENTION

Considering the above deficiencies in prior art, the present disclosure provides a rabies vaccine composition, comprising or consisting of: a) inactivated purified rabies virus (referred as IPRV), b) PIKA adjuvant, and c) human serum albumin (referred as HSA). In some embodiments, the rabies vaccine composition comprises 0.2 IU to 4.0 IU per unit dose IPRV, 250 µg to 5000 µg per unit dose PIKA adjuvant, and 0.1% to 0.9% by concentration of HSA (before freeze drying or after reconstitution).

The unit dose suitable for present vaccine composition is prepared into a volume which is selected from the group consisting of 0.1 ml, 0.15 ml, 0.2 ml, 0.5 ml, 1.0 ml, 1.5 ml, 2.0 ml, and the range between any two of the following volumes: 0.1 ml, 0.15 ml, 0.2 ml, 0.5 ml, 1.0 ml, 1.5 ml, and 2.0 ml. It is understood that too large and too small administration volume lead to inconvenience in clinical practice, when applied to human subject. Therefore, the unit dose for human adult may typically be prepared into 0.5 ml or 1.0 ml for injection (liquid form or after reconstitute of freeze-dried powder form), and 0.15 ml or 0.2 ml for intra-nasal form application.

In some embodiments, the amount of IPRV is selected from the group consisting of 0.2 IU, 0.5 IU, 1.0 IU, 1.5 IU, 2.0 IU, 2.5 IU, 3.0 IU, 3.5 IU, 4.0 IU per unit dose, and the range between any two of the following IU values: 0.2 IU, 0.5 IU, 1.0 IU, 1.5 IU, 2.0 IU, 2.5 IU, 3.0 IU, 3.5 IU, and 4.0 IU. In some embodiments, the amount of IPRV is from 0.2 IU to 4.0 IU per unit dose. In some particular embodiments, the amount of IPRV is selected from the group consisting of 1.0 IU, 1.5 IU, 2.0 IU, 2.5 IU per unit dose, and the range between any two of the following per unit doses: 1.0 IU, 1.5 IU, 2.0 IU, and 2.5 IU per unit dose. In one particular embodiment, the amount of IPRV for human adult may be from 1.0 IU to 2.0 IU per unit dose, e.g., 1.0 IU or 2.0 IU per unit dose. In other embodiments, when applied to children, the amount of IPRV per unit dose may be reduced; for example, the amount of IPRV may be from 0.5 IU to 1.0 IU per unit dose, e.g., 0.5 IU or 1.0 IU per unit dose. In some particular embodiments, the concentration of said IPRV is between 0.05 IU/ml and 40.0 IU/ml, such as 0.05, 0.1, 0.15, 0.2, 0.5, 1.0, 2.0, 3.0, 4.0, 5.0, 10, 15, 20, 25, 30, 35, 40 IU/ml, and the range between any two of the following concentrations: 0.05, 0.1, 0.15, 0.2, 0.5, 1.0, 2.0, 3.0, 4.0, 5.0, 10, 15, 20, 25, 30, 35, and 40 IU/ml.

In some embodiments, the amount of PIKA adjuvant suitable for present vaccine composition is selected from the group consisting of 250 µg, 500 µg, 1000 µg, 1500 µg, 2000 µg, 3000 µg, 4000 µg, 5000 µg per unit dose, and the range between any two of the following amounts: 250 µg, 500 sg, 1000 µg, 1500 µg, 2000 µg, 3000 µg, 4000 µg, 5000 µg per unit dose. In some particular embodiments, for human subject administration, the amount of PIKA adjuvant is from 250 µg to 4000 µg per unit dose.

In some particular embodiments, the amount of PIKA adjuvant is selected from the group consisting of 500 µg, 1000 µg, 1500 µg, 2000 µg, 2500 µg per unit dose, and the value between any two of the following amounts: 500 µg, 1000 µg, 1500 µg, 2000 µg, 2500 µg per unit dose. In other embodiments, when applied to children, the amount of PIKA adjuvant per unit dose may be reduced, for example, the amount of PIKA adjuvant is selected from the group consisting of 250 µg, 500 µg, 750 µg 1,000 µg, 1250 µg per unit dose, and the value between any two of the following amounts: 250 µg, 500 µg, 750 µg, 1000 µg and 1250 µg per unit dose.

Any suitable PIKA adjuvant can be used in the vaccine composition of present disclosure. PIKA is a synthetic chemical analogue of a dsRNA that has been shown to be a TLR3 agonist through pre-clinical studies. PIKA adjuvant is composed of Poly I:C, an antibiotic (e.g., kanamycin) and a positive ion (e.g., calcium chloride). It is soluble in aqueous solution with pH between 6.0 and 8.0. Unless otherwise indicated, the PIKA adjuvant suitable for the rabies vaccine composition of present disclosure is the PIKA adjuvant disclosed in WO2006/131023, incorporated by reference herein in its entirety. In related embodiments, the PIKA adjuvant are heterogeneous for molecular weight, where the molecular weight is from about 66,000 to 1,200,000 Daltons, or from about 66,000 to 660,000 Daltons, or from about 138,000 to 660,000 Daltons, or from about 150,000 to 660,000 Daltons, or from about 138,000 to 1,200,000 Daltons, or from about 150,000 to 1,200,000 Daltons, or from about 300,000 to 1,200,000 Daltons, or from about 300,000 to 660,000 Daltons, or from about 337,000 to 660,000 Daltons, or from about 337,000 to 1,200,000 Daltons, or from about 500,000 to 1,200,000 Daltons, or from about 500,000 to 2,000,000 Daltons.

In related embodiments, the PIKA adjuvant molecules in the rabies vaccine composition have an average molecular weight equal to or greater than 100,000 Daltons, or equal to or greater than 120,000 Daltons, or equal to or greater than 138,000 Daltons, or equal to or greater than 150,000 Daltons, or equal to or greater than 250,000 Daltons, or equal to or greater than 300,000 Daltons, or equal to or greater than 337,000 Daltons, or equal to or greater than 500,000 Daltons, or equal to or greater than 750,000 Daltons, or equal to or greater than 1,000,000 Daltons, or equal to or greater than 1,200,000 Daltons, or equal to or greater than 1,500,000 Daltons, or equal to or greater than 2,000,000 Daltons.

In some embodiments, the ratio of IPRV to PIKA adjuvant is selected from the group consisting of: 1 IU/100 μg, 1 IU/125 μg, 1 IU/200 μg, 1 IU/250 g, 1 IU/300 μg, 1 IU/350 μg, 1 IU/400 μg, 1 IU/450 μg, 1 IU/500 g, 1 IU/550 g, 1 IU/600 μg, 1 IU/700 μg, 1 IU/800 μg, 1 IU/1000 μg, 1 IU/1500 g, 1 IU/2000 μg and the ratio between any above two ratios. In a particular embodiment, the ratio of IPRV to PIKA adjuvant is 1 IU/500 μg. In one particular embodiment, the amount of IPRV is 2.0 IU per unit dose, and the amount of PIKA adjuvant is 1000 jpg per unit dose. In another particular embodiment, the amount of IPRV is 4.0 IU per unit dose, and the amount of PIKA adjuvant is 2000 μg per unit dose. In another particular embodiment, the amount of IPRV is 3.0 IU per unit dose, and the amount of PIKA adjuvant is 1000 jig per unit dose. In still another particular embodiment, the amount of IPRV is 1.0 IU per unit dose, and the amount of PIKA adjuvant is 1000 μg per unit dose. In still another particular embodiment, the amount of IPRV is 1.0 IU per unit dose, and the amount of PIKA adjuvant is 2000 μg per unit dose.

In some embodiments, the vaccine composition of present disclosure further comprises pharmaceutical acceptable buffer. In some embodiments, pharmaceutical acceptable buffer is selected from the group consisting of: PBS, acetate, tris-hydroxymethyl aminomethane, bicarbonates, and carbonates. In some embodiments, the pH of buffer is selected from the group consisting of: 7.00, 7.05, 7.1, 7.15, 7.2, 7.25, 7.30, 7.35, 7.40, 7.45, 7.50, 7.55, 7.60, 7.65, 7.70, 7.75, 7.80, 7.85, 7.90, 7.95, 8.00 and the range between any two of the following pH values: 7.00, 7.05, 7.1, 7.15, 7.2, 7.25, 7.30, 7.35, 7.40, 7.45, 7.50, 7.55, 7.60, 7.65, 7.70, 7.75, 7.80, 7.85, 7.90, 7.95, and 8.00. In some particular embodiments, the buffer is PBS, and the pH of PBS buffer is selected from the group consisting of: 7.3, 7.4, 7.5, and the range between any above two values.

In some embodiments, the amount of HSA suitable for present vaccine composition is selected from the group consisting of 0.15%, 0.20%, 0.25%, 0.30%, 0.35%, 0.40%, 0.45%, 0.50%, 0.60% by concentration (before freeze drying or after reconstitution), and the value between any above two values. Human albumin is added in rabies vaccine as a stabilizer for the processing, freeze-dry process and storage. Those skilled persons in the art will understand that albumin is a known allergen to some animals, but human albumin alone is an approved drug for human use and it can be safely used in human applications.

In some embodiments, the rabies vaccine composition according to present disclosure further comprises maltose. In some embodiments, the amount of maltose is between 1.0% and 6.0% by concentration (before freeze drying or after reconstitution). In some embodiments, the amount of maltose is selected from the group consisting of 1.0%, 1.5%, 2.0%, 2.5%, 3.0%, 3.5%, 4.0%, 4.5%, 5.0%, 6.0% by concentration, and the range between any above two values. In some particular embodiments, the amount of maltose is 5.0% by concentration.

In some embodiments, the rabies vaccine composition according to present disclosure does not comprise gelatin.

Unless otherwise indicated, any available rabies antigen can be used to prepare the rabies vaccine composition according to present disclosure. WHO approved several strains of rabies virus for vaccine production, including but not limited to Pitman-Moore strain (PM), Pasteur virus strains (PV), challenge virus strain (CVS), low-egg-passage (LEP) and high-egg-passage (HEP) strain from Flury chick embryo-adapted strain, Evelyn Rokitniki Abelseth (ERA) strain of Street-Alabama-Dufferin (SAD) virus and different SAD variants. These approved strains of virus are adapted in brain tissue culture, chick or duck embryo, primary cell line (such as hamster kidney cell line), human diploid cell, or continuous cell line (such as Vero cell line). The virus strains above can be used to manufacture vaccines after inactivation and purification. In some embodiments, the IPRV is selected from the group consisting of CTN strain, aG strain, Pitman-Moore (PM) strain and Pasteur virus strain (PV) strain. In some particular embodiments, the IPRV is selected from the group consisting of CTN-1 strain, Pitman-Moore L503 strain and PV-2061 strain.

In some particular embodiments, the IPRV is prepared in Vero cell or primary hamster kidney (PHK) cell. The IPRV is produced by propagating the fixed virus strain into Vero cell or PHK cell. After collecting the supernatant of culture medium, the virus is harvested, concentrated, inactivated, purified and stored as the antigen.

Unless otherwise indicated, the rabies vaccine composition according to present disclosure can be prepared in a liquid form, including but not limited to solution or suspension. In some other particular embodiments, the rabies vaccine composition is prepared as solid form, such as freeze-dried or lyophilized form.

In some particular embodiments, the rabies vaccine composition according to present disclosure, comprising or consisting of: 2.0 IU/ml IPRV, 1.0 mg/ml PIKA adjuvant and 0.3% HSA. In some other particular embodiments, the rabies vaccine composition according to present disclosure, comprising or consisting of: 2.0 IU/ml IPRV, 2.0 mg/ml PIKA adjuvant, 0.3% HSA. In some other particular embodiments, the rabies vaccine composition according to present disclosure, comprising or consisting of: 1.0 IU/ml IPRV, 2.0 mg/ml PIKA adjuvant and 0.3% HSA; or 1.5 IU/ml IPRV, 2.0 mg/ml PIKA adjuvant and 0.3% HSA; or 2.0 IU/ml IPRV, 2.0 mg/ml PIKA adjuvant and 0.5% HSA; or 4.0 IU/ml IPRV, 1.0 mg/ml PIKA adjuvant and 0.5% HSA.

The present disclosure also provides a pharmaceutical kit, comprising or consisting of: a) the rabies vaccine composition of present disclosure, b) a container, such as a vial or an ampoule, c) an instruction for use, and optionally d) water for injection. In some particular embodiments, for the convenience of transportation and storage, the pharmaceutical kit is prepared into a lyophilized form. Therefore, a pharmaceutical kit comprises or consists of a) lyophilized rabies vaccine composition, b) a vial which holds the lyophilized rabies vaccine composition, and c) an instruction for use. When necessary, water for injection can be incorporated into the pharmaceutical kit to reconstitute the liquid rabies vaccine composition before use. In some particular embodiments, the instruction for use suggests the following administration regimen: 2-2-1 regimen for post exposure protection and/or 2-1 regimen for prophylaxis, wherein said 2-2-1 regimen refers to 2 unit doses administered on day 0, 2 unit doses administered on day 3 and 1 unit dose administered on day 7; wherein 2-1 regimen refers to 2 unit doses administered on day 0, and 1 unit dose administered on day 7. In another particular embodiment, the instruction for use suggests the following administration regimen: 2-2-2 regimen for post exposure protection, wherein said 2-2-2 regimen refers to 2 unit doses administered on days 0, 3, and 7 respectively. In another particular embodiment, the instruction for use suggests the following administration regimen: 1-1-1 regimen for post exposure protection, wherein said 1-1-1 regimen refers to 1 unit doses administered on days 0, 3, and 7 respectively.

The present disclosure also provides a method for inducing an immune response to rabies virus by administering to a host the rabies vaccine composition containing PIKA adjuvant according to present disclosure. The host can be a human being or non-human animal. The administration can be done by injection or by inhalation.

Also disclosed herein is a rabies vaccine composition for use in a method of medical treatment. In particular, the disclosure provides a rabies vaccine composition for use in a method of treatment or prevention of rabies. The rabies vaccine composition may be for use in a method of inducing an immune response to a rabies virus. The rabies vaccine composition is useful in the methods of medical treatment and prevention, and methods of inducing an immune response disclosed herein.

The disclosure also provides for the use of a rabies vaccine composition in the manufacture of a medicament for the treatment or prophylaxis of rabies. In one aspect, present disclosure provides the use of rabies vaccine composition according to present disclosure in the manufacture of a medicament for the treatment or prophylaxis of rabies caused by rabies virus infection. In another aspect, present disclosure also provides a rabies vaccine composition, for the treatment or prophylaxis of rabies caused by rabies virus infection. The medicament is useful in the methods of medical treatment and prevention, and methods of inducing an immune response disclosed herein.

In prior art, there are two commonly used intramuscular vaccine schedules: one is Essen schedule which involves 5 injections given at days 0, 3, 7, 14, and 28 post exposure; the other is Zagreb schedule which involves 4 injections wherein two injections are administered on day 0 at different sites, and another two additional injections are given on day 7 and day 21. However, the existing administration regimen is usually limited, due to extensive immunization schedule requiring 5 clinical visits and the low titers of antibodies production in early stage of immunization. In contrast, present disclosure provides a method for treatment of rabies virus infection with an accelerated schedule. In some particular embodiments, the method comprises a step of administering the rabies vaccine composition of present disclosure to a host, wherein said host has been exposed to rabies virus. In some particular embodiments, the host is human. In some other particular embodiments, the host is non-human animal, such as rodent, dog and monkey.

The present disclosure provides an accelerated administration regimen, wherein a vaccine composition is administered to a host for 5 times within 7 days post exposure of rabies virus, with day 0 being the day the host was exposed to the rabies virus. In some particular embodiments, the vaccine composition is administered to a host based on the following regimen: 1) a first administration on 0 day post exposure, 2) a second administration on 0 day post exposure, 3) a third administration on 2 or 3 day post exposure, 4) a fourth administration on 2 or 3 day post exposure, and 5) a fifth administration on 6 or 7 day post exposure, respectively. As an alternative, in some other particular embodiments, the vaccine composition is administered to a host based on the following regimen: a $1^{st}$ and a $2^{nd}$ administration on 0 day post exposure; a $3^{rd}$ and a $4^{th}$ administration on 2 or 3 day post exposure; and a $5^{th}$ and/or $6^{th}$ administration on 7 day post exposure, respectively. The rabies vaccine compositions disclosed herein may be administered according to the accelerated administration regimen.

In another aspect, present disclosure also provides a method for prophylaxis of rabies caused by rabies virus infection, and a rabies vaccine composition for use in such a method. In some particular embodiments, the method comprises a step of administering the rabies vaccine composition of present disclosure to a host, wherein said host is not exposed to rabies virus. In some particular embodiments, the host is human. In some other particular embodiments, the host is non-human animal, such as rodent, dog and monkey. In some particular embodiments, the rabies vaccine composition of present disclosure is administered to a host for 3 times within 7 days. In some particular embodiments, the rabies vaccine composition of present disclosure is administered to a host based on the following regimen: 1) a first administration on day 0; 2) a second administration on day 0; and 3) a third administration on day 7, respectively. Prophylaxis or prevention includes treatment of a subject, particularly a human, who does not have the disease, or is asymptomatic for the disease. Particularly preferred methods of preventing rabies, or prophylaxis, are pre-exposure prophylaxis (PEP) methods, in which the vaccine is administered before the subject is exposed to, or at risk of exposure to, live rabies virus. The subject may have been identified as predisposed to, or at risk of developing, the disease. In the case or rabies, the subject may have been determined to be predisposed to, or at risk of developing, rabies. For example, because they have visited or intend to visit a country or location in which rabies is known to be present, or because they work with the virus, or with animals.

In the context of present disclosure, the administration is carried out by parenteral injection, intramuscular injection, intraperitoneal injection, intravenous injection, subcutaneous injection, topical delivery, transdermal delivery and intradermal delivery. In some particular embodiments, the administration for animal can be carried out by intraperitoneal injection. In some other particular embodiments, the administration for human is carried out by intramuscular injection or intravenous injection. In another particular embodiment, the administration is carried out by inhalation, rectal delivery, nasal delivery, oral delivery (including inhalation).

BRIEF DESCRIPTION OF THE DRAWINGS

FIG. 1. PIKA rabies vaccine toxicity data, and dose conversion calculation.

FIG. 2. Production process of IPRV antigen.

DETAILED DESCRIPTION OF EXEMPLARY EMBODIMENTS OF THE INVENTION

Figure 3:
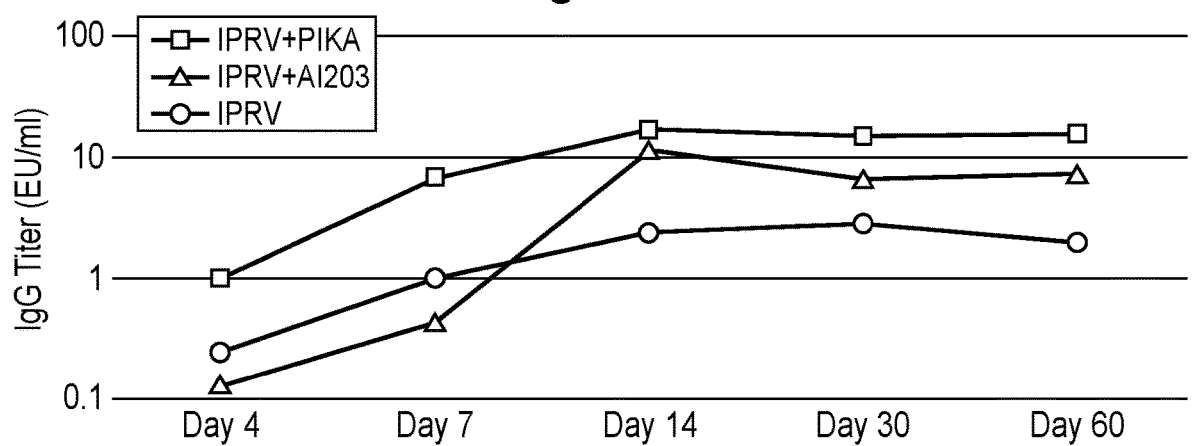
FIG. 3. Antibody induction by various immunization compositions.

The present disclosure may be understood more readily by reference to the following detailed description of certain embodiments and the examples included herein. Throughout this disclosure, where publications are referenced, the disclosures of these publications are hereby incorporated by reference in their entireties into this disclosure in order to more fully describe the state of art to which this disclosure pertains.

Before the present disclosure is further described, it is to be understood that this disclosure is not limited to particular embodiments described, as such may vary. It is also to be understood that the terminology used herein is for the purpose of describing particular embodiments only, and is not intended to be limiting, since the scope of the present disclosure will be limited only by the appended claims. Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. It must be noted that as used herein and in the appended claims, the singular forms "a," "an," and "the" include plural referents unless the context clearly dictates otherwise.

DEFINITIONS OF TERMS

The term "adjuvant" as used herein, refers to any substance or mixture of substances that increases or diversifies the immune response of a host to an antigenic compound.

"PIKA" refers to a composition comprising poly I:C, an antibiotic (e.g., kanamycin), and a positive ion (e.g., calcium). PIKA exhibits characteristics of an adjuvant with reduced adverse side effects (e.g., reduced toxicity) relative to for example PICKCa and greater potency (e.g., stimulates an enhanced immune response) relative to for example Av-PICKCa.

"PIKA rabies vaccine" refers to a rabies vaccine composition containing the IPRV antigen and PIKA adjuvant. The terms "PIKA rabies vaccine", "PIKA rabies vaccine composition", "vaccine composition containing PIKA", "rabies vaccine composition containing PIKA adjuvant", "PIKA-adjuvanted rabies vaccine" and "PIKA-adjuvanted vaccine composition" can be used interchangeably.

The term "animal" includes humans and all domestic and wild mammals, including, without limitation, cattle, horses, cows, swine, sheep, goats, dogs, cats, rodents, monkeys and the like.

"Antigen" refers to a substance which when administered induces an immune response, for example the formation of antibodies, including antibodies that specifically bind the antigen. Two of the characteristic features of antigens are their immunogenicity that is their capacity to induce an immune response in vivo, and their antigenicity that is their capacity to be selectively recognized by the antibodies whose origins are the antigens.

The terms "cell-mediated immunity" and "cell-mediated immune response" refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The expression "enhanced immune response" or similar means that the immune response is elevated, improved or enhanced to the benefit of the host, relative to the prior immune response status, for example before the administration of an immunogenic composition of the invention.

The terms "humoral immunity" and "humoral immune response" refer to the form of immunity in which antibody molecules are produced in response to antigenic stimulation.

The term "immune response" refers to any response to an antigenic compound by the immune system of a vertebrate subject. Exemplary immune responses include, but are not limited to cellular as well as local and systemic humoral immunity, such as CTL responses, including antigen-specific induction of CD8+ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is, stimulated, initiated, or induced.

The term "potentiating an immune response" refers to a pre-existing immune response that is improved, furthered, supplemented, amplified, enhanced, increased, or prolonged.

The term "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in subject, particularly a human, and includes: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease. The term "prophylaxis" or "preventing" and the like are used herein to generally refer to treatment given to prevent or slow the development of disease.

The term "mixing" includes any method to combine the components of the composition; such methods include, but are not limited to, blending, dispensing, dissolving, emulsifying, coagulating, suspending, or otherwise physically combining the components of the composition.

The term "unit dose" as used herein refers to physically discrete units suitable as unitary dosages for human and animal subjects, each unit containing a predetermined quantity of present composition calculated in an amount sufficient to produce the desired effect. In any cases, the term "unit dose" should not be understood as the volume of vaccine composition contained in a container (such as a vial).

The Rabies Vaccine Composition

The current disclosure provides a rabies vaccine composition, comprising or consisting of: a) inactivated purified rabies virus (referred as IPRV), b) PIKA adjuvant, and c) human serum albumin (referred as HSA). In some embodiments, the rabies vaccine composition comprises 0.2 IU to 4.0 IU per unit dose IPRV, 250 µg to 5000 µg per unit dose PIKA adjuvant, and 0.1% to 0.9% by concentration HSA, where the concentration is defined as weight in volume (w/v) during formulation, i.e. 0.1% HSA refers to 1 mg HSA content in 1 ml of total volume. During the freeze-drying process, water is removed by sublimating from the solid phase to the gas phase. The same amount of HSA as measured by weight is retained in the freeze-drying powder and the concentration in term of w/v will be restored after reconstitution.

The unit dose suitable for present vaccine composition is prepared into a volume which is selected from the group consisting of 0.1 ml, 0.15 ml, 0.2 ml, 0.5 ml, 1.0 ml, 1.5 ml, 2.0 ml, and the range between any two of the following volumes: 0.1 ml, 0.15 ml, 0.2 ml, 0.5 ml, 1.0 ml, 1.5 ml, and 2.0 ml. It is understood that too large and too small administration volume leads to inconvenience in clinical practice, when applied to human subject. Therefore, the unit dose for human adult may typically be prepared into 0.5 ml or 1.0 ml for injection (liquid form or after reconstitute of freeze-dried powder form), and 0.15 ml or 0.2 ml for intra-nasal form application.

In certain embodiments, the amount of IPRV is selected from the group consisting of 0.2 IU, 0.5 IU, 1.0 IU, 1.5 IU, 2.0 IU, 2.5 IU, 3.0 IU, 3.5 IU, 4.0 IU per unit dose, and the range between any two of the following IU values: 0.2 IU, 0.5 IU, 1.0 IU, 1.5 IU, 2.0 IU, 2.5 IU, 3.0 IU, 3.5 IU, and 4.0 IU. In some embodiments, the amount of IPRV is from 0.2 IU to 4.0 IU per unit dose. In some particular embodiments, the amount of IPRV is selected from the group consisting of 1.0 IU, 1.5 IU, 2.0 IU, 2.5 IU per unit dose, and the range between any two of the following per unit doses: 1.0 IU, 1.5 IU, 2.0 IU, and 2.5 IU per unit dose. In one particular embodiment, the amount of IPRV for human adult may be from 1.0 to 2.0 IU per unit dose e.g., 1.0 IU or 2.0 IU per unit dose. In other embodiments, when applied to children, the amount of IPRV per unit dose may be reduced; for example, the amount of IPRV may be from 0.5 IU to 1.0 IU per unit dose, e.g., 0.5 IU or 1.0 IU per unit dose. In some particular embodiments, the concentration of said IPRV is between 0.05 IU/ml and 40.0 IU/ml, such as 0.05, 0.1, 0.15, 0.2, 0.5, 1.0, 2.0, 3.0, 4.0, 5.0, 10, 15, 20, 25, 30, 35, 40 IU/ml, and the range between any two of the following concentrations: 0.05, 0.1, 0.15, 0.2, 0.5, 1.0, 2.0, 3.0, 4.0, 5.0, 10, 15, 20, 25, 30, 35, and 40 IU/ml.

In certain embodiments, the amount of PIKA adjuvant suitable for present vaccine composition is selected from the group consisting of 250 µg, 500 µg, 1000 µg, 1500 µg, 2000 µg, 3000 µg, 4000 µg, 5000 µg per unit dose, and the range between any two of the following amounts: 250 µg, 500 µg, 1000 µg, 1500 µg, 2000 µg, 3000 µg, 4000 µg, 5000 µg per unit dose. In some particular embodiments, for human adult subject administration, the amount of PIKA adjuvant is between 250 µg and 4000 µg per unit dose. In some particular embodiments, the amount of PIKA adjuvant is selected from the group consisting of 500 µg, 1000 µg, 1500 µg, 2000 µg, 2500 µg per unit dose, and the range between any two of the following amounts: 500 µg, 1000 µg, 1500 µg, 2000 µg, 2500 µg per unit dose. In other embodiments, when applied to children, the amount of PIKA adjuvant per unit dose may be reduced, for example, the amount of PIKA adjuvant is selected from the group consisting of 250 µg, 500 µg, 750 µg, 1000 µg, 1250 µg per unit dose, and the range between any two of the following amounts: 250 µg, 500 µg, 750 µg, 1000 µg, and 1250 µg per unit dose.

Of the many adjuvants available for use in mammals, only a few, including aluminium hydroxide and aluminium phosphate, have been widely used in rabies vaccine for humans. Other adjuvants have been rejected for use in humans because they cause severe local or systematic reactions. For example, Freund's complete adjuvant which contains mineral oil, are non-metabolizable and causes cancer in laboratory animals. Recently, rabies vaccine without aluminium salt has been developed. It could generate comparable titers of rabies neutralising antibodies as the aluminium-adjuvanted vaccines.

PIKA adjuvant, which composed of Poly I:C, an antibiotic (e.g., kanamycin), and a positive ion (e.g., calcium) as disclosed in WO2006/131023, incorporated by reference herein in its entirety, has been approved to enhance the immunogenicity of rabies antigen in animal studies. In related embodiments, the PIKA adjuvant are heterogeneous for molecular weight, where the molecular weight is from about 66,000 to 1,200,000 Daltons, or from about 66,000 to 660,000 Daltons, or from about 138,000 to 660,000 Daltons, or from about 138,000 to 1,200,000 Daltons, or from about 150,000 to 1,200,000 Daltons, or from about 150,000 to 660,000 Daltons, or from about 300,000 to 1,200,000 Daltons, or from about 300,000 to 660,000 Daltons, or from about 337,000 to 660,000 Daltons, or from about 337,000 to 1,200,000 Daltons, or from about 500,000 to 1,200,000 Daltons, or from about 500,000 to 2,000,000 Daltons.

In related embodiments, the PIKA adjuvant molecules in the vaccine composition have an average molecular weight equal to or greater than 100,000 Daltons, or equal to or greater than 120,000 Daltons, or equal to or greater than 138,000 Daltons, or equal to or greater than 150,000 Daltons, or equal to or greater than 250,000 Daltons, or equal to or greater than 300,000 Daltons, or equal to or greater than 337,000 Daltons, or equal to or greater than 500,000 Daltons, or equal to or greater than 750,000 Daltons, or equal to or greater than 1,000,000 Daltons, or equal to or greater than 1,200,000 Daltons, or equal to or greater than 1,500,000 Daltons, or equal to or greater than 2,000,000 Daltons.

Any suitable PIKA adjuvant can be used in the vaccine composition of present disclosure. In some embodiments, the molecular weight of PIKA adjuvant is within the range from 66,000 Daltons to 1,200,000 Daltons. In a preferred embodiment, the molecular weight of PIKA adjuvant is 66,000 Daltons to 660,000 Daltons.

In some embodiments, the ratio of IPRV to PIKA adjuvant is selected from the group consisting of: 1 IU/100 µg, 1 IU/125 g, 1 IU/200 µg, 1 IU/250 µg, 1 IU/300 µg, 1 IU/350 g, 1 IU/400 µg, 1 IU/450 µg, 1 IU/500 g, 1 IU/550 µg, 1 IU/600 g, 1 IU/700 µg, 1 IU/800 µg, 1 IU/1000 µg, 1 IU/1500 g, 1 IU/2000 µg, and the ratio between any two of the following ratios: 1 IU/100 µg, 1 IU/125 µg, 1 IU/200 µg, 1 IU/250 µg, 1 IU/300 µg, 1 IU/350 µg, 1 IU/400 g, 1 IU/450 µg, 1 IU/500 µg, 1 IU/550 µg, 1 IU/600 µg, 1 IU/700 g, 1 IU/800 µg, 1 IU/1000 µg, 1 IU/1500 µg, and 1 IU/2000 g. In one particular embodiment, the ratio of IPRV to PIKA adjuvant is 1 IU/500 µg. In one particular embodiment, the amount of IPRV is 2.0 IU per unit dose, and the amount of PIKA adjuvant is 1000 µg per unit dose. In another particular embodiment, the amount of IPRV is 4.0 IU per unit dose, and the amount of PIKA adjuvant is 2000 µg per unit dose. In another particular embodiment, the amount of IPRV is 3.0 IU per unit dose, and the amount of PIKA adjuvant is 1000 g per unit dose. In still another particular embodiment, the amount of IPRV is 1.0 IU per unit dose, and the amount of PIKA adjuvant is 1000 μg per unit dose. In still another particular embodiment, the amount of IPRV is 1.0 IU per unit dose, and the amount of PIKA adjuvant is 2000 μg per unit dose.

It is known in the art that, according to WHO standard, potency of the inactivated purified rabies vaccine with or without adjuvant greater than 2.5 IU, base on NIH potency test or variation of NIH test, is suitable for prophylaxis or post-exposure treatment of rabies virus infection. In actual production, vaccine potency is usually greater than 4.5 IU at production and the potency decreases along with storage time. Within the shelf-life of the vaccine, potency should not decrease below 2.5 IU.

The low antigen dose used in the current disclosure can be potentiated by the addition of PIKA adjuvant to produce highly effective protection immunity in mice and monkey upon vaccination (see examples 1-3 and 6). Animal study also shows that the rabies composition containing PIKA adjuvant could induce earlier and higher titers of specific antibody production (see example 1).

Thus, the resulting rabies vaccine composition achieves higher potency with lower amount of antigen content. In effect, the rabies vaccine composition with lower antigen dose reduces production cost and potential side effect, while the vaccine is effective in inducing an immune response against rabies viral infection.

Moreover, we have found that a resulting PIKA-adjuvanted rabies vaccine shows strong thermostability when above described amount of HSA and maltose is added without the presence of geletin. HSA and maltose are known as a stabilizing agent for rabies vaccine; however, it has never been known that a combination thereof at a specific amount, the vaccine composition according to present disclosure exhibits thermostability.

Manufacturing Process of the Rabies Vaccine Composition

Unless otherwise indicated, any available rabies antigen can be used to prepare the rabies vaccine composition according to present disclosure. The most commonly used strains of rabies virus for vaccine production, including but not limited to CTN-1 strain, aG strain, Pitman Moore (PM) strain, the Kissling strain of Challenge Virus Standard (CVS), or the Flury low egg passage (LEP) or high-egg-passage (HEP), fixed Evelyn Rokitniki Abelseth (ERA) strain of Street-Alabama-Dufferin (SAD) virus and different SAD variants.

In some particular embodiment, the inactivated purified rabies vaccine antigen is obtained from aG rabies virus strain cultured in hamster kidney cell line (PHK). The virus is prepared and perfused to PHK cell. The cells were then cultured in virus culture medium before they are harvested to give the virus harvest solution.

In another particular embodiment of the current disclosure, the inactivated purified rabies vaccine antigen is obtained from CTN-1 rabies virus strain cultured in Vero cell line. The CTN-1 rabies virus strain is inoculated and perfused into Vero cell line, and then harvested to give the viral solution.

The harvested viral solution then goes through concentrating and inactivation process to produce the inactivated antigen. The inactivated purified virus solution was then obtained through column chromatography after the addition of HSA (See FIG. 1 for an illustration of the production process). In some particular embodiment, the amount of HSA suitable for present vaccine composition is selected from the group consisting of 0.1%, 0.15%, 0.2%, 0.25%, 0.3%, 0.35%, 0.4%, 0.45%, 0.5% by concentration, and the value between any above two values.

In some embodiment, the PIKA adjuvant is manufactured from single-strand polynucleotide polymers, PolyI and PolyC, followed by the addition of mono-kanamycin sulfate (Kanamycin) and calcium chloride ($CaCl_2$)) to give the final adjuvant. In some embodiments, the pH of PIKA adjuvant is selected from the group consisting of: 6.0, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0 7.05, 7.1, 7.15, 7.2, 7.25, 7.3, 7.35, 7.4, 7.45, 7.5, 7.55, 7.6, 7.65, 7.7, 7.75, 7.8, 7.85, 7.9 7.95, 8.0 and the value between any two of the above pH values: 6.0, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0 7.05, 7.1, 7.15, 7.2, 7.25, 7.3, 7.35, 7.4, 7.45, 7.5, 7.55, 7.6, 7.65, 7.7, 7.75, 7.8, 7.85, 7.9 7.95, and 8.0. In some particular embodiments, the pH of PIKA adjuvant is from pH6.0 to pH8.0.

In some embodiment, the Rabies vaccine composition is produced by combining the IPRV and the PIKA adjuvant in a phosphate buffer solution. The IPRV and PIKA adjuvant are mixed under a pH selecting from a group of: 6.0, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0 7.05, 7.1, 7.15, 7.2, 7.25, 7.3, 7.35, 7.4, 7.45, 7.5, 7.55, 7.6, 7.65, 7.7, 7.75, 7.8, 7.85, 7.9 7.95, 8.0 and the value between any two of the following pH values: 6.0, 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0 7.05, 7.1, 7.15, 7.2, 7.25, 7.3, 7.35, 7.4, 7.45, 7.5, 7.55, 7.6, 7.65, 7.7, 7.75, 7.8, 7.85, 7.9 7.95, and 8.0.

In some embodiments, the rabies vaccine composition according to present disclosure does not comprise gelatin.

In some embodiments, the final product comprises: 2.0 IU/ml IPRV, 1.0 mg/ml PIKA adjuvant, 5.0% maltose, and 0.3% HSA. In some other particular embodiments, the rabies vaccine composition according to present disclosure, comprising or consisting of: 2.0 IU/ml IPRV, 2.0 mg/ml PIKA adjuvant, 0.3% HSA. In some other particular embodiments, the rabies vaccine composition according to present disclosure, comprising or consisting of: 1.0 IU/ml IPRV, 2.0 mg/ml PIKA adjuvant and 0.3% HSA; or 1.5 IU/ml IPRV, 2.0 mg/ml PIKA adjuvant and 0.3% HSA; or 2.0 IU/ml IPRV, 2.0 mg/ml PIKA adjuvant and 0.5% HSA; or 4.0 IU/ml IPRV, 1.0 mg/ml PIKA adjuvant and 0.5% HSA.

The final product is filled into sterilized vial with filling volume of 1 ml/vial to form a unit dose, and then capped. Those skilled persons will understand that filling volume of 1 ml/vial involves operational error. Therefore, the filling volume of 1 ml/vial may range from 0.90 to 1.20 ml/vial, such as from 1.10 to 1.12 ml/vial.

It should be noted that the filling volume is not limited to 1 ml/vial, and can be any suitable value selecting from a group of: 0.1 ml, 0.2 ml, 0.3 ml, 0.4 ml, 0.5 ml, 0.6 ml, 0.7 ml, 0.8 ml, 0.9 ml, 1.0 ml, 1.2 ml, 1.5 ml, 2.0 ml/vial, and any volume between any above two values. In a preferred embodiment, when applied to human adult subject, too large and too small administration volume lead to inconvenience in clinical practice, thus the administration volume for human is 1 ml. Therefore, the composition in present disclosure is prepared in a form of 1 ml/vial. When applied to child or other type of subjects, filling volume and unit dose can be adjusted accordingly.

In some embodiments, the liquid form of rabies vaccine can also be prepared into its corresponding solid form. In such situation, the liquid form composition is further subjected to lyophilization. Such solid form of rabies vaccine is packaged together with water for injection optionally. The vaccine is reconstituted before use, the final volume for injection is selected from a group of: 0.1 ml, 0.15 ml, 0.2 ml, 0.25 ml, 0.3 ml, 0.4 ml, 0.5 ml, 0.6 ml, 0.7 ml, 0.8 ml, 0.9 ml, 1.0 ml, 1.2 ml, 1.5 ml, 2.0 ml, and any volume between any two values.

In some embodiment, the liquid form of rabies vaccine of suitable concentration is prepared for intranasal application. In such situation, the volume of administering the rabies vaccine composition ranges from 0.05 ml to 0.1 ml, 0.1 ml to 0.15 ml, 0.15 ml to 0.2 ml, 0.2 ml to 0.25 ml, 0.25 ml to 0.3 ml, 0.3 ml to 0.35 ml, 0.35 ml to 0.4 ml, 0.4 ml to 0.45 ml, 0.45 ml to 0.5 ml and any range between any two of the following volumes: 0.05 ml to 0.1 ml, 0.1 ml to 0.15 ml, 0.15 ml to 0.2 ml, 0.2 ml to 0.25 ml, 0.25 ml to 0.3 ml, 0.3 ml to 0.35 ml, 0.35 ml to 0.4 ml, 0.4 ml to 0.45 ml, 0.45 ml to 0.5 ml. The concentration of said IPRV is from 0.05 IU/ml to 40.0 IU/ml, such as 0.05, 0.1, 0.15, 0.2, 0.5, 1.0, 2.0, 3.0, 4.0, 5.0, 10, 15, 20, 25, 30, 35, 40 IU/ml, and the value between any above two values.

Safety of the Rabies Vaccine Composition

In principle, the way of assessing drug safety is an approach of risk identification and risk mitigation. For first-in-human applications, the safety can be assessed on chosen animal species used for testing. The conversion from animal toxicity data to maximum recommended safe dose on human may include the following steps: 1) determine the No Observed Adverse Effect Level (NOAEL), 2) convert the NOAEL to Human Equivalent Dose (HED) in most relevant testing species, and 3) apply a suitable safety factor (e.g. 10).

According to FDA guideline for Industry—Estimating the Maximum Safe Starting Dose in Initial Clinical Trials for Therapeutics in Adult Healthy Volunteers, the human equivalent dose can be calculated from the pre-clinical animal studies selected from a model animals described in the table below:

TABLE 1

Conversion of Animal Doses to Human Equivalent Doses

| Species | Reference Body Weight (kg) | Working Weight Range (kg) | Divide Animal Dose By | Multiply Animal Dose By |
|---|---|---|---|---|
| Human | 60 | — | — | — |
| Child | 20 | — | — | — |
| Mouse | 0.02 | 0.011-0.034 | 12.3 | 0.081 |
| Hamster | 0.08 | 0.047-0.157 | 7.4 | 0.135 |
| Rat | 0.15 | 0.080-0.270 | 6.2 | 0.162 |
| Ferret | 0.3 | 0.160-0.540 | 5.3 | 0.189 |
| Guinea pig | 0.4 | 0.208-0.700 | 4.6 | 0.216 |
| Rabbit | 1.8 | 0.9-3.0 | 3.1 | 0.324 |
| Dog | 10 | 5-17 | 1.8 | 0.541 |
| Primates: | | | | |
| Monkeys | 3 | 1.4-4.9 | 3.1 | 0.324 |
| Marmoset | 0.35 | 0.140-0.720 | 6.2 | 0.162 |
| Squirrel monkey | 0.6 | 0.290-0.970 | 5.3 | 0.189 |
| Baboon | 12 | 7-23 | 1.8 | 0.541 |
| Micro-pig | 20 | 10-33 | 1.4 | 0.73 |
| Mini-pig | 40 | 25-64 | 1.1 | 0.946 |

Any above animals suitable for the evaluating the safety of the investigational product can be selected as the model animal for study. Typically, at least one type of experimental rodent animal and at least one type of experimental primate animal should be selected for evaluation before human application. Test animals should be tested for acute toxicity with single application and long-term toxicity with repeated application.

The currently disclosed rabies vaccine composition containing PIKA adjuvant is tested in both rodents and primate to show excellent safety profile (see details of safety tests in examples 5 and 7).

Stability of the Rabies Vaccine Composition

Vaccines are usually transported or stored before use. Normal shelf-life for vaccine ranges from 1 to 3 years. Therefore, thermostability of vaccine is required to ensure vaccine potency at the time of administration. Due to high prevalence of rabies disease, vaccines are commonly distributed to tropical countries where there are no refrigerated distribution systems. In these areas, the vaccine preparations supplied must have thermostability at high temperature.

The currently disclosed rabies vaccine composition is tested both under 2 to 8° C. and 37° C. for extended period of time to confirm the thermostability (detail refers to example 13).

Kits

In some embodiments, a subject kit comprises a rabies vaccine composition in a sterile liquid (e.g., aqueous) formulation, where the formulation is sterile, and is provided in a sterile container, a sterile vial, a sterile ampoule, or a sterile syringe.

In some embodiments, a subject kit comprises a rabies vaccine composition, lyophilized and in a sterile container; and a container comprising a sterile liquid for reconstitution of the lyophilized composition. In some embodiments, the kit further comprises instructions for reconstitution of the lyophilized composition.

A subject kit in some embodiments will further include instructions for use, including e.g., dosage amounts and dosage frequencies. Instructions are in some embodiments printed directly on the kit. In other embodiments, instructions are printed material provided as a package insert. Instructions can also be provided in other media, e.g., compact disc, a digital versatile disk, and the like.

The present disclosure also provides a pharmaceutical kit, comprising or consisting of: a) the rabies vaccine composition of present disclosure, b) a container, such as a vial or an ampoule, c) an instruction for use, and optionally d) water for injection. In some particular embodiments, for the convenience of transportation and storage, the pharmaceutical kit is prepared into a lyophilized form. Therefore, the a pharmaceutical kit comprises or consists of a) lyophilized rabies vaccine composition, b) a vial which holds the lyophilized rabies vaccine composition, and c) an instruction for use. When necessary, water for injection can be incorporated into the pharmaceutical kit to reconstitute the liquid rabies vaccine composition before use. In some particular embodiments, the instruction for use suggests the following administration regimen: 2-2-1 regimen, 2-2-2 regimen, 1-1-1 regimen, and/or 2-1 regimen, wherein said 2-2-1 regimen refers to 2 unit dose administered on days 0, 2 unit dose administered on days 3 and 1 unit dose administered on days 7; wherein 2-2-2 regimen refers to 2 unit dose administered on days 0, 3 and 7; wherein 1-1-1 regimen refers to 1 unit dose administered on days 0, 3 and 7; wherein 2-1 regimen refers to 2 unit dose administered on days 0, and 1 unit dose administered on days 7.

Method of Administration

The present disclosure also provides a method for inducing an immune response to rabies virus by administering to a host the rabies vaccine composition containing PIKA adjuvant according to present disclosure. The host can be a human being or non-human animal. The administration can be done by injection or by inhalation.

Also disclosed herein is a rabies vaccine composition for use in a method of medical treatment. In particular, the disclosure provides a rabies vaccine composition for use in a method of treatment or prevention of rabies. The rabies vaccine composition may be for use in a method of inducing an immune response to a rabies virus. The rabies vaccine composition is useful in the methods of medical treatment and prevention, and methods of inducing an immune response disclosed herein.

The disclosure also provides for the use of a rabies vaccine composition in the manufacture of a medicament for the treatment or prophylaxis of rabies. In one aspect, present disclosure provides the use of rabies vaccine composition according to present disclosure in the manufacture of a medicament for the treatment or prophylaxis of rabies caused by rabies virus infection. In another aspect, present disclosure also provides a rabies vaccine composition, for the treatment or prophylaxis of rabies caused by rabies virus infection. The medicament is useful in the methods of medical treatment and prevention, and methods of inducing an immune response disclosed herein.

In prior art, there are two commonly used intramuscular vaccine schedules: one is Essen schedule which involves 5 injections given at days 0, 3, 7, 14, and 28 post exposure; the other is Zagreb schedule which involves 4 injections wherein two injections are administered on day 0 at different sites, and another two additional injections are given on day 7 and day 21. However, the existing administration regimen is usually limited, due to extensive immunization schedule requiring 5 clinical visits and the low titers of antibodies production in early stage of immunization. Considering this, present disclosure provides a method for treatment of rabies virus infection with an accelerated schedule. In some particular embodiments, the method comprises a step of administering the rabies vaccine composition of present disclosure to a host, wherein said host is has been exposed to rabies virus. In some particular embodiments, the host is human. In some other particular embodiments, the host is non-human animal, such as rodent, dog and monkey.

In some particular embodiments, present disclosure provides an accelerated administration regimen, wherein the rabies vaccine composition of present disclosure is administered to a host for 5 times within 7 days post exposure of rabies virus. In some particular embodiments, the rabies vaccine composition of present disclosure is administered to a host based on the following regimen: 1) a first administration on 0 day post exposure, 2) a second administration on 0 day post exposure, 3) a third administration on 2 or 3 day post exposure, 4) a fourth administration on 2 or 3 day post exposure, and 5) a fifth administration on 6 or 7 day post exposure, optionally, 6) a sixth administration on 6 or 7 day post exposure, respectively. As an alternative, in some other particular embodiments, the rabies vaccine composition of present disclosure is administered to a host based on the following regimen: a $1^{st}$ and a $2^{nd}$ administration on 0 day post exposure; a $3^{rd}$ and a $4^{th}$ administration on 2 or 3 day post exposure; and a $5^{th}$ and/or $6^{th}$ administration on 7 day post exposure, respectively.

In another aspect, present disclosure also provides a method for prophylaxis of rabies virus infection, and a rabies vaccine composition for use in such a method. In some particular embodiments, the method comprises a step of administering the rabies vaccine composition of present disclosure to a host, wherein said host is not exposed to rabies virus. In some particular embodiments, the host is human. In some other particular embodiments, the host is non-human animal, such as rodent, dog and monkey. In some particular embodiments, the rabies vaccine composition of present disclosure is administered to a host for 3 times within 7 days. In some particular embodiments, the rabies vaccine composition of present disclosure is administered to a host based on the following regimen: 1) a first administration on day 0; 2) a second administration on day 0; and 3) a third administration on day 7, respectively. Prophylaxis or prevention includes treatment of a subject, particularly a human, who does not have the disease, or is asymptomatic for the disease. Particularly preferred methods of preventing rabies, or prophylaxis, are pre-exposure prophylaxis (PEP) methods, in which the vaccine is administered before the subject is exposed to, or at risk of exposure to, live rabies virus. The subject may have been identified as predisposed to, or at risk of developing, the disease. In the case or rabies, the subject may have been determined to be predisposed to, or at risk of developing, rabies. For example, because they have visited or intend to visit a country or location in which rabies is known to be present, or because they work with the virus, or with animals.

In the context of present disclosure, the administration is carried out by parenteral injection, intramuscular injection, intraperitoneal injection, intravenous injection, subcutaneous injection, topical delivery, transdermal delivery and intradermal delivery. In some particular embodiment, the administration for animal can be carried out by intraperitoneal injection. In some other particular embodiments, the administration for human is carried out by intramuscular injection or intravenous injection. In another particular embodiment, the administration is carried out by inhalation, rectal delivery, nasal delivery, oral delivery (including inhalation).

EXAMPLES

Example 1. Humoral Immune Response and Viral Challenge Test in Mice

Protocols:
Protocol 1: Humoral Immune Response
OF1 mice are administered with IPRV (PV strain produced in BHK 21 cell, 0.2 IU) with or without PIKA (75 g) on days 0, 3, 7, 14 and 30. Blood samples are taken 5 times over the 60-day period post immunization, and tested for virus neutralizing antibodies by Rapid Fluorescent Focus Inhibition Test (RFFIT), and also assayed for IgG, IgM using ELISA.

Protocol 2: Viral Challenge Test
OF1 mice are infected subcutaneously with wild rabies virus ($5\times10^6$ icLD50) after which they are administered PIKA adjuvant alone (50 µg), high or low doses of IPRV (0.1 or 0.2 IU, PV strain) without adjuvant, with 50 μg $Al_2O_3$, or with 50 μg PIKA at 6 hours, 3 and 7 days post infection. Survival rates of the mice are observed.

Summary of Findings:

(1) The humoral immune response (i.e. antibody titer using RFFIT test) is observed to be higher in animals receiving the rabies vaccine composition with PIKA. While PIKA adjuvant vaccine composition could induce higher titers of IgG and IgM production as early as 4 days post immunization. Aluminum adjuvant vaccine composition decreases antibody titer in early stage. The titers of IgG antibodies generated by the rabies vaccine composition with or without adjuvant are presented in FIG. 3.

(2) Under lethal dose viral challenge test where 95% mice died without vaccination or with Aluminum adjuvanted vaccine, and PIKA rabies vaccine composition provided 90% protection even when sub-optimal level of IPRV (0.1 IU) was used. All the mice immunized with optimal level of IPRV (0.2 IU) with PIKA adjuvant survived, while only 30% of the mice survived when immunized with optimal level of IPRV and aluminum adjuvant.

As a conclusion, the rabies vaccine composition comprising PIKA adjuvant could induce 6-7 times higher titers of neutralizing antibody after immunization compared to traditional aluminum adjuvant vaccine. The high IgG level is maintained over a 60-day observing period, which provided a long-lasting humoral protection post immunisation.

The earlier increase in neutralizing antibody could also provide more effective protection for patients receiving post-exposure vaccination. A more direct conclusion can be drawn, as all PIKA adjuvant rabies vaccine immunized mice survive from lethal viral challenge.

Example 2. Cell-Mediated Immune Response in Mice 2.1. T Cell Growth Factor IL-2 Induction and Splenocyte Proliferation In Vitro Protocol: C3H mice are immunized with PBS control, IPRV (0.1 IU) with or without PIKA adjuvant (10 g), subcutaneously. A week later, mice were sacrificed and Splenocytes were isolated to evaluate IL-2 production using Gillis method. Briefly, splenocytes were cultured and stimulated with control, IPRV, PIKA adjuvant or ConA. Supernatant was then harvested after 24 hours and filtered before IL-2 titration. The supernatant was added into CTLL cell culture, whose growth is dependent upon the presence of IL-2. IL-2 production is titrated by measuring the CTLL cell proliferation. Furthermore, $^3$H-thymidine was added to determine the splenocyte proliferation by measuring $^3$H-thymidine incorporation after stimulation.

Summary of findings: the rabies vaccine composition containing 0.1 IU IPRV and 10 µg of PIKA adjuvant could enhance IL-2 production and splenocyte proliferation. When used for in vitro stimulation, PIKA adjuvant alone induces weak IL-2 production and high splenocytes proliferation, indicating PIKA adjuvant involves in multiple cellular mechanisms to activate splenocytes besides T helper cells which require IL-2.

2.2. Macrophage Activation

Protocol: 3 groups of Kunming mice (weighted 20 g on average) are immunized with saline control, 0.1 IU IPRV with or without PIKA adjuvant (10 µg). Mice received intraperitoneal administered with above compositions at days 0, 3, 7 and 14. Peritoneal macrophages were collected and isolated 4 hours after each immunization for microscopy inspection. Macrophage phagocytic activity was counted and present in table below:

TABLE 2

Macrophage phagocytosis index

| Group | Day 0 | Day 3 | Day 7 | Day 14 |
|---|---|---|---|---|
| Saline control | 11% (0.13) | 31% (0.47) | 34% (0.49) | 6% (0.12) |
| IPRV | 4% (0.09) | 10% (0.12) | 27% (0.45) | 12% (0.14) |
| IPRV + PIKA | 82% (1.48) | 70% (1.9) | 66% (2.46) | 45% (1.14) |

Note:
Percentage indicating number of macrophages with phagocytosis activity over number of macrophages without phagocytosis activity; Number in braket indicating number of red blood cells engulfed by each macrophage.

Table 2 shows that PIKA adjuvant could enhance macrophage activities while IPRV alone inhibits macrophage activation.

2.3. Increase Interferon-γ (IFN-γ) Production

Rabies antigen (0.1 or 0.2 IU) produced in PHK cell with or without PIKA adjuvant (10 or 50 µg) against standard. BALB/c mice were immunized intraperitoneally with one or two doses of the above three compositions at day 0 or days 0 and 7 respectively. Mice were sacrificed 7 days post immunization (i.e. day 7 for mice receiving one dose, and day 14 for mice receiving two doses). Splenocytes were isolated to test IFN-γ production using ELISPOT.

Result: Rabies vaccine composition containing IPRV produced in PHK cell and PIKA adjuvant induced IFN-γ production in mice as early as 7 days after the first dose. The group without PIKA adjuvant does not have significant IFN-γ production. In mice receiving two doses of the rabies vaccine composition containing IPRV produced in PHK cell and PIKA adjuvant (50 µg) generated 2-fold higher IFN-γ than the standard group. Even with suboptimal level of PIKA adjuvant (10 µg), mice generate significant level of IFN-γ after the second dose. This shown that PIKA adjuvanted rabies vaccine composition could provide T-cell mediated immune response soon after immunization and increase up to 14 days post immunization.

The rabies vaccine composition containing suboptimal level of IPRV (0.1 IU) and (10 µg) adjuvant of above two example is equivalent to human-use composition of 24.39 IU IPRV and 2,439 µg PIKA adjuvant per unit dose (refer to FIG. 1 and table 1 for conversion). This is indicative for a human dose about 2.4 IU IPRV and 240 µg PIKA adjuvant, when a commonly used safety factor 10 is applied. For the optimal level of IPRV IPRV (0.2 IU) and (50 jig or 75 µg) adjuvant is used, the indicative dose for a human is about 4 IU IPRV and 1,200 µg or PIKA adjuvant.

Example 3. Adjuvant Potentiating IPRV Antigen Potency

Same batch of IPRV is used to prepare non-adjuvanted, PIKA adjuvanted and Aluminum adjuvanted vaccine compositions. Mice were immunized with different preparation of rabies vaccine compositions and challenged with CVS strain intracerebrally. $ED_{50}$ is measured using NIH method. Amount of adjuvant added and resulting $ED_{50}$ is presented in Table 3:

TABLE 3

Rabies vaccine composition potency test

| | Adjuvant amount (µg) | | |
|---|---|---|---|
| | Day 0 | Day 7 | $ED_{50}$ |
| IPRV (0.2 IU) | 0 | 0 | 221 |
| IPRV (0.2 IU) + PIKA | 100 | 100 | 22 |
| IPRV (0.2 IU) + Aluminum | 1000 | 1000 | 132 |

Results: $ED_{50}$ of PIKA adjuvanted vaccine compositions decreased about 10 fold while Aluminium adjuvanted vaccine compositions only decreased about 1 fold. As a conclusion, PIKA adjuvant has significant better potentiating effect to rabies antigen compare to Aluminium adjuvant.

Example 4. Vaccine Formulation Optimization

Existing rabies vaccine usually contains IPRV antigen greater than 4.5 IU. However, for PIKA rabies vaccine in present disclosure, the antigen level proposed is <4.5 IU. This was recommended based on pre-clinical studies, including the test with golden hamster on post exposure protection test (example 5). Results showed that PIKA rabies vaccine composition containing 2 IU antigen had a better protection than the commercially available vaccine composition containing >4.5 IU antigen. As such, we have tested various antigen levels from 0.25 to 3.0 IU in the final dose form; this is to potentially reduce the side effect and also reduce the cost of vaccine while still maintaining a good level of efficacy with the addition of PIKA adjuvant. For test purpose, the dose of PIKA is kept constant at 1.0 mg. In addition, the influence on the efficacy of vaccine based on different amount of PIKA and concentrations of human albumin was also studied.

4.1. The Efficacy of Vaccines with Different Titer of IPRV Antigen Added

While other components (PIKA, HSA and Maltose) of the rabies vaccine were kept constant, the immunoprotective efficacy of the vaccine compositions with different titer of antigen is examined in Table 4 below:

TABLE 4

Immunoprotective efficacies of vaccines with different titers of antigen

| | Formula | | | | Result |
|---|---|---|---|---|---|
| Group | IPRV Antigen (IU/dose) | PIKA (mg/dose) | HSA (%) | Mal (%) | Potency (IU/dose) |
| V-1 | 0.25 | 1.0 | 0 | 5.0 | 1.7 |
| V-2 | 0.5 | 1.0 | 0 | 5.0 | 3.4 |
| V-3 | 1.0 | 1.0 | 0 | 5.0 | 3.0 |
| V-4 | 1.5 | 1.0 | 0 | 5.0 | 3.3 |
| V-5 | 2.0 | 1.0 | 0 | 5.0 | 4.7 |
| V-6 | 2.5 | 1.0 | 0 | 5.0 | 3.7 |
| V-7 | 3.0 | 1.0 | 0 | 5.0 | 5.1 |

Analysis: Vaccine potency with the antigen titers between 0.5 and 3.0 IU/dose (a relative quantity of international unit) added were always more than 2.5 IU/dose (a relative potency international unit), which met the standard requirements for rabies vaccine recommended by WHO, as well as in Pharmacopoeia of the People's Republic of China, 2010 Edition, Volume 3.

4.2. The Efficacy Ofvaccine Compositions with Different Amount of PIKA Adjuvant Added With amount of IPRV, HSA and Maltose kept constant, the immunoprotective efficacy of the vaccines with different amount of PIKA adjuvant were examined in Table 5:

TABLE 5

Immunoprotective efficacies of vaccines with different titers of antigen

| | Formula | | | | Result |
|---|---|---|---|---|---|
| Group | IPRV Antigen (IU/dose) | PIKA (mg/dose) | HSA (%) | Mal (%) | Potency (IU/dose) |
| P-1 | 2.0 | 0.25 | 0 | 5.0 | 6.8 |
| P-2 | 2.0 | 0.5 | 0 | 5.0 | 6.0 |
| P-3 | 2.0 | 0.75 | 0 | 5.0 | 5.6 |
| P-4 | 2.0 | 1.0 | 0 | 5.0 | 4.7 |
| P-5 | 2.0 | 1.25 | 0 | 5.0 | 4.4 |
| P-6 | 2.0 | 1.5 | 0 | 5.0 | 6.6 |
| P-7 | 2.0 | 2.0 | 0 | 5.0 | 8.9 |

Analysis: When the amount of PIKA adjuvant added is between 0.25 and 2.0 μg/dose the efficacies of resulting rabies composition were always more than 2.5 IU/dose, which met the standard requirements for rabies vaccine recommended by WHO. When used as anti-viral drug, up to 4 mg of PIKA is approved to be used repeatedly in human subjects with good therapeutic effects and was well tolerated. Moreover, 1.0 mg of PIKA adjuvant has been used in human phase I trial to potentiate the rabies antigen with good prophylaxis efficacy. Therefore, the amount of PIKA adjuvant ranges from 0.25 to 4 mg of PIKA should be safe and effective to be added into the final formulation.

4.3. The Influence of HSA Concentration on the Stability of Rabies Vaccine

The stability of freeze-dried PIKA rabies vaccine under various HSA concentrations was examined in Table 6 below:

TABLE 6

Influence of HSA concentration on the stability of rabies vaccine

| | Formula | | | | Result (vaccine potency) | |
|---|---|---|---|---|---|---|
| Group | IPRV Antigen (IU/dose) | PIKA (mg/dose) | HSA (%) | Mal (%) | Potency at month 0 (IU/dose) | Accelerated Stability (IU/dose) |
| H-1 | 2.0 | 1.0 | 0 | 5.0 | 4.7 | 4.9 |
| H-2 | 2.0 | 1.0 | 0.1 | 5.0 | 5.5 | 6.9 |
| H-3 | 2.0 | 1.0 | 0.2 | 5.0 | 7.8 | 4.6 |
| H-4 | 2.0 | 1.0 | 0.3 | 5.0 | 7.9 | 10.5 |
| H-5 | 2.0 | 1.0 | 0.5 | 5.0 | 10.9 | 7.2 |
| H-6 | 2.0 | 1.0 | 1.0 | 5.0 | 9.1 | 5.5 |

Analysis: With the rest of the concentrations (Antigen, PIKA and Maltose) kept constant, the potency of vaccine and the accelerated stability were always more than 2.5 IU/dose, when the concentration of HSA was between 0 and 1.0%. These results meet the standard requirements of WHO for similar products in the market.

Thus, an balanced formulation of the rabies vaccine composition containing PIKA adjuvant would comprise IPRV-2.0 IU; PIKA adjuvant-1.0 mg; human albumin-0.3% (3 mg in 1 ml final vaccine composition before freeze drying or after reconstitution); and maltose-5% (i.e. 50 mg in 1 ml final vaccine composition before freeze drying or after reconstitution).

Example 5. Golden Hamster Post Exposure Protection Test

Protocol: 7 groups of 7 to 8 weeks old female golden hamsters, 100 to 150 g body weight (15 per group) were infected with 0.1 ml of 50 $LD_{50}$ wild rabies virus BD06 strain. The vaccine was administered intramuscularly at the hind legs. Survival rates of the animals were observed for 45 days. The grouping information is as follows:

Group 1: Saline control with 1-1-1-1-1 immunization schedule (i.e. a single dose injection 2 hours and 3, 7, 14, 28 days post exposure);

Group 2: A commercially available rabies vaccine (flurry LEP strain IPRV produced in chick embryo cells, >2.5 IU) with the same immunization schedule as group 1;

Group 3: Human Rabies Immunoglobulin at 2 sites i.e. half of 1.5 IU administered at right hind leg and another half administered at left hind leg 2 hours post exposure;

Group 4: the rabies vaccine composition containing CTN-1 strain IPRV produced in Vero cell line and PIKA adjuvant with 1-1-1-1-1 immunization schedule;

Group 5: the rabies vaccine composition containing CTN-1 strain IPRV produced in Vero cell line and PIKA adjuvant with 2-2-1 immunization schedule (i.e. double dose injection 2 hours, 2 days post exposure and a single dose injection 7 days post exposure).

Group 6: the rabies vaccine composition containing aG strain IPRV produced in PHK cell and PIKA adjuvant with 1-1-1-1-1 immunization schedule;

Group 7: the rabies vaccine composition containing aG strain IPRV produced in PHK cell and PIKA adjuvant with 2-2-1 immunization schedule (i.e. double dose injection 2 hours, 2 days post exposure and a single dose injection 7 days post exposure).

Compositions: the rabies vaccine composition used in Groups 4-5 containing 2.0 IU/ml IPRV, 1000 µg/ml PIKA adjuvant, 5% maltose, and 0.3% HSA, injected with unit dose of 0.1 ml, is equivalent to human-use dose by body weight composition of 10.8 IU IPRV and 5405 µg PIKA adjuvant per unit dose (refer to FIG. 1 and table 1 for conversion). After dividing with a safety factor of 10, result of this study is indicative to human application with about 1.0 IU IPRV and 500 µg PIKA.

Summary of findings: The commercially available rabies vaccine with standard immunization schedule only provided limited protection after post exposure protection test, whereas PIKA rabies vaccine composition could provide significantly better protection using the same regimen. Both PIKA rabies vaccine composition with enhanced regimen and the passive immunization with immunoglobulin protected 80% of the subjects (p<0.005). The protection rate for all testing groups was shown below:

TABLE 7

Golden hamsters' exposure protection test

| Grouping | Total No. of Subjects | No. of Subject Survived | No. of Subject Died | Death Rate (%) | Protection Rate (%) |
|---|---|---|---|---|---|
| 1 Saline control | 15 | 1 | 14 | 93.3 | / |
| 2 Novartis rabies vaccine (1-1-1-1-1) | 15 | 3 | 12 | 80.0 | 20.0 |
| 3 Immunoglobulin | 15 | 12 | 3 | 20.0 | 80.0 |
| 4 PIKA rabies vaccine (1-1-1-1-1) Vero cell | 15 | 10 | 5 | 33.3 | 66.7 |
| 5 PIKA rabies vaccine (2-2-1) Vero cell | 15 | 12 | 3 | 20.0 | 80.0 |
| 6 PIKA rabies vaccine (1-1-1-1-1) PHK cell | 15 | 7 | 8 | 53.3 | 46.7 |
| 7 PIKA rabies vaccine (2-2-1) PHK cell | 15 | 10 | 5 | 33.3 | 66.7 |

In conclusion, commercially available vaccine only provided limited protection, whereas presently described rabies vaccine composition provides significantly stronger protection. By using accelerated 2-2-1 regimen (i.e. double dose for the first two injections), rabies vaccine composition containing IPRV CTN-1 strain produced in Vero cell and PIKA adjuvant could provide similar level of protection as of Human rabies immunoglobulin.

Example 6. Mice Post Exposure Protection Test

Protocol: Four groups of mice (20 per group) exposed to high dose of CQ92 rabies virus were immunized with 0.06 ml commercially available rabies vaccine from various source, the rabies vaccine composition containing PIKA adjuvant or PBS as a negative control on days 0, 3, 6 and 9.

Composition: the rabies vaccine composition containing PIKA adjuvant, used in Groups 1 containing 1.5 IU/ml PM strain IPRV produced in PHK cell, 1000 µg/ml PIKA adjuvant, and 0.2% HSA, injected with unit dose of 0.06 ml, is equivalent to human-use composition of 21.95 IU IPRV and 14,634 pig PIKA adjuvant per unit dose (refer to FIG. 1 and table 1 for conversion). This is indicative for a human dose about 2 IU IPRV and 1,500 µg PIKA adjuvant, when a commonly used safety factor 10 is applied.

The mice were then observed for 21 days after the last injection. Survival rates are shown in Table 8 below:

TABLE 8

Mice post exposure protection test

| Grouping | Antigen dose (IU/ml) | Adjuvant dose (µg/ml) | No of Surviving Subjects | No. of Subjects died | Survival Rate |
|---|---|---|---|---|---|
| 1 PIKA rabies vaccine | 1.5 | 1,000 PIKA | 16 | 4 | 80% |
| 2 Comparator vaccine (France) | 2.5 | — | 2 | 18 | 10% |
| 3 Comparator vaccine (China) | 2.5 | 1,000 Alu | 3 | 17 | 15% |
| 4 PBS Control | — | — | 4 | 16 | 20% |

Summary of Findings: Mice from the comparator vaccine groups confer similar level of protection as the control group under lethal dose viral challenge. Rabies vaccine with PIKA confirms an 80% protection for the mice in the post exposure protection test when lower dose of antigen is used. In short, the composition in present disclosure greatly enhances rabies vaccine protection rate against lethal dose viral infection in mice with a reduced antigen level.

Example 7. Acute Toxicity Study in Rodents

Protocol: Five groups of 3-5 weeks old Kunming (KM) mice, 20 mice (10 male and 10 female, weighted 20 g on average in each group), were administered a single dose of 0.2 ml composition set out in table below:

TABLE 9

Rodent Acute Toxicity

| Group | Test Composition | Injection Volume | PIKA Adjuvant | Rabies Antigen |
|---|---|---|---|---|
| 1 | 0.1M PBS Control | 0.2 ml | — | — |
| 2 | PIKA adjuvant alone | 0.2 ml | 200 µg | — |
| 3 | PIKA adjuvant | 0.2 ml | 200 µg | — |
| 4 | PIKA Rabies Vaccine composition (½ dose) | 0.2 ml | 100 µg | 0.2 IU |
| 5 | PIKA Rabies Vaccine composition (full dose) | 0.2 ml | 200 µg | 0.4 IU |

The mice were then monitored 4 hours after drug administration for toxic reactions, death and abnormal clinical symptoms, followed by daily observation for 14 days. Body weight was measured prior to the first injection and on days 1, 4, 7, 11, and 14 post injection. Food intake was recorded on days 1, 7 and 14 post injection. The mice were sacrificed on day 14 followed by macro-pathology examination on the following organs: heart, liver, spleen, lung, kidney, adrenal gland, brain, stomach, intestine, trachea, testis, epididymis, uterus, ovary, thymus gland, lymph nodes (including cervical lymph nodes, mesenteric lymph nodes and iliac Peyer lymph nodes), left and right posterior limb muscle.

Results: Animals in the study group did not show significant variations in food intake and body weight compared to control groups. No abnormal clinical symptoms were observed 14 days after drug administration while all animals survived the maximum dose of drug administered without observable toxic reactions and abnormalities during organ visual examination.

In conclusion, the rabies vaccine composition containing PIKA adjuvant is well tolerated in KM mice to the maximum dose of 0.4 IU rabies antigen with 200 µg PIKA. Mice receiving rabies vaccine composition containing 0.4 IU IPRV and 200 µg PIKA adjuvant has margin of safety (MOS) of 150 to 300 fold when 2 IU IPRV and 1000 µg PIKA is to be used for human application. The calculation of MOS is presented in Table below:

TABLE 10

Kunming Mice Acute Toxicity - Margin of Safety Calculation

| Study Groups | Volume (weight)/ injection | Effective Dose Dose (ml/kg BW) | MOS |
|---|---|---|---|
| Human dose | 2.0 ml (60 kgBW)/injection | 0.03 | / |
| ½ dose in mice | 0.2 ml (20 gBW)/injection | 5.00 | 150 |
| Full dose in mice | 0.2 ml (20 gBW)/injection | 10.00 | 300 |

Example 8. Allergic Reaction Test in Rodents

Protocol: Seven groups of 299.6 g to 339.1 g Dunkin-Hartley guinea pigs, 6 animals (3 male and 3 female) per group, were administered intramuscularly three doses of the compositions set out in Table 11 below every two days. Animals were challenged intravenously with double the immunization dose 10 to 14 days post immunization:

TABLE 11

Rodent allergic reaction - immunization and challenge plan

| Group | Test Composition | Immunisation (0.5 ml/injection, 3 injections) IPRV Dose | Immunisation (0.5 ml/injection, 3 injections) PIKA Dose | Challenge (1 injection) Dose | Challenge (1 injection) Volume |
|---|---|---|---|---|---|
| 1 | 0.9% NaCl negative control | — | — | — | 1 ml |
| 2 | BSA positive control | — | — | 40 mg | 1 ml |
| 3 | PIKA adjuvant alone | — | 1.5 mg | 1.0 mg | 1 ml |
| 4 | PIKA adjuvant + 0.3% HSA | — | 1.5 mg | 1.0 mg | 1 ml |
| 5 | IPRV (Vero Cell) without HSA | 3 IU/ml | — | 2 IU/ 1.0 mg | 1 ml |
| 6 | IPRV (PHK Cell) without HSA | 3 IU/ml | — | 2 IU/ 1.0 mg | 1 ml |
| 7 | PIKA + IPRV (Vero Cell, +0.3% HSA (low dose) | 1.5 IU/ml | 1.5 mg | 1 IU/ 0.5 mg | 1 ml |
| 7.1 | PIKA + IPRV (Vero Cell, without HSA, low dose) | 1.5 IU/ml | 1.5 mg | 1 IU/ 1.5 mg | 1 ml |
| 8 | PIKA + IPRV (PHK cell, +0.3% HSA (high dose) | 3 IU/ml | 1.5 mg | 2 IU/ 1.0 mg | 1 ml |
| 8.1 | PIKA + IPRV (PHK cell, without HSA, high dose) | 3 IU/ml | 1.5 mg | 2 IU/ 1.0 mg | 1 ml |

Results: All animals in negative control group showed no sign of allergic reaction, while animals in positive control group started to show allergic reaction within 1 minute after challenge. Symptoms including: scratching nose, cough, purpura, ataxia and spasticity. Animal in PIKA adjuvant or the rabies vaccine composition group without human albumin did not show any obvious allergic reaction during immunization and challenge, while PIKA adjuvant and the rabies vaccine composition groups containing human albumin showed different degree of allergic reaction. Two pairs of animals (1 male and 1 female) taken from group 6 and 7 (with 0.3% HSA) were administered with additional 1 ml (the challenging volume) low-dose or high-dose PIKA rabies vaccine without human albumin respectively (marked as Group 6.1 and 7.1). No allergic reaction is observed with the additional challenged test in absence of human albumin.

As a conclusion, the rabies vaccine composition containing PIKA adjuvant and PIKA adjuvant without the addition of human albumin are non-allergic and well tolerated in test animals after multiple doses of up to 3 IU of rabies antigen and 1,500 µg PIKA adjuvant through intramuscular route. The MOS for the rabies vaccine composition used in the allergic reaction is 25 fold for low dose group and 50 fold for high dose group.

The calculated is presented below:

TABLE 12

Guinea Pigs Allergic Reaction - Margin of Safety Calculation

| Study Groups | Volume/ injection | Total volume/ Body weight | Effective Dose Total Dose/ kg BW | MOS |
|---|---|---|---|---|
| Human Dose | 1.0 ml | 5.0 ml/60 kgBW | 0.03 | / |
| PIKA adjuvant | 0.5 ml | 2.5 ml/0.3 kgBW | 8.30 | 50 |
| Low-dose group | 0.5 ml (½ diluted) | 2.5 ml/0.3 kgBW | 4.17 | 25 |
| High-dose group | 0.5 ml (standard) | 2.5 ml/0.3 kgBW | 8.30 | 50 |

Example 9. Repeat Dose Chronic Toxicity and Efficacy Study in Primates

Protocol for safety evaluation: Four groups of 2-3 year old rhesus monkeys with 8 animals per group (4 male and 4 female) between 2.5 kg to 4.0 kg in weight were administered with PIKA Rabies Vaccine composition at escalating doses (two groups), PIKA alone or 0.9% NaCl (control group) by injecting to the deltoid muscle 5 times within a 6-week period, i.e. days 0, 2, 7, 28 and 42. The first two injections were administered at two sites (i.e. double dose), see Table 13 below.

TABLE 13

Primate Chronic Toxicity Study Groups

| Group | Test Composition | Per Dose | | | Volume | |
|---|---|---|---|---|---|---|
| | | PIKA (µg) | IPRV (IU) | Control | Per injection | Total |
| 1 | Control | / | / | 0.9% NaCl | 0.5 ml | 3.5 ml |
| 3 | 1000 µg/ml PIKA adjuvant + 0.3% albumin | 1,000 | / | / | 0.5 ml | 3.5 ml |
| 4 | 500 µg/ml PIKA adjuvant + 1 IU/ml IPRV + 0.3% HSA (low dose) | 500 | 1 IU | / | 0.5 ml | 3.5 ml |
| 5 | 1000 µg/ml PIKA adjuvant + 2 IU/ml IPRV + 0.3% HSA(high dose) | 1,000 | 2 IU | / | 1.0 ml | 7.0 ml |

The injection site and systemic clinical symptoms of the monkeys were observed several times before and after immunization. Blood samples were obtained 4 times on days −0 (i.e. animal quarantine period), 44 and 70. Blood samples were used for hematology, blood coagulation, and serum biochemistry tests.

Protocol for efficacy: Humoral immune responses and potency was measured on days 44 and 70. Two male and two female monkeys were sacrificed on days 45 and 70 for histological examination. Organs were weighed, sliced and fixed before staining for light microscope examination.

Results:

1. No abnormal injection-site or systemic clinical symptoms were observed in all animals administered PIKA adjuvant or PIKA Rabies Vaccine composition. All values in the test were within the range of data center background, no significant changes were reported. Weight of various organs showed no significant difference between control and other testing groups.

Figure 4:
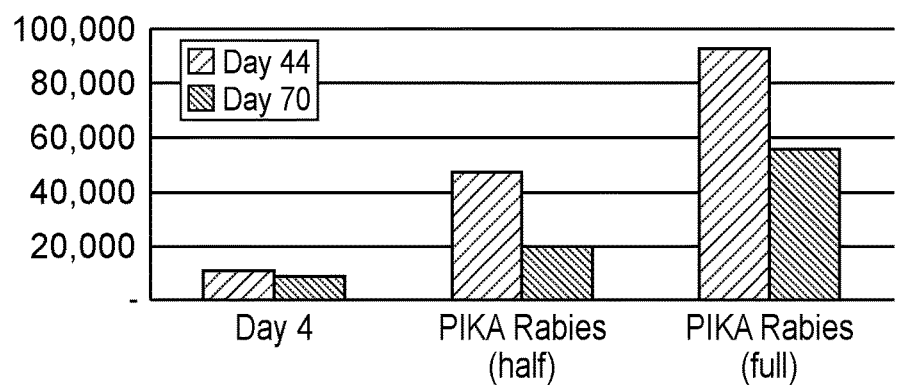
FIG. 4. PIKA rabies vaccine induced serum IgG titer in immunized monkey.
Figure 5:
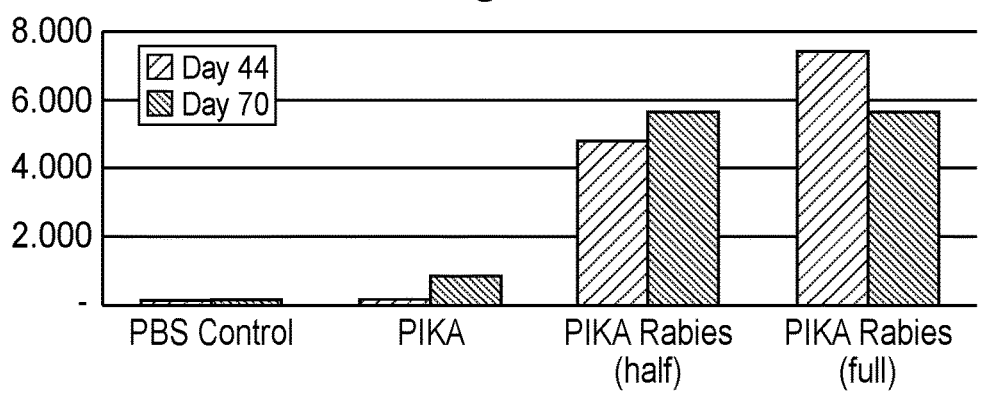
FIG. 5. PIKA rabies vaccine induced neutralizing antibody in immunized monkey (Y-axis Unit IU).

2. The humoral immune responses represented by geometric mean titers of rabies-specific IgG and neutralizing antibody potency in blood sera were evaluated using ELISA or FAVN test respectively. Tables 14-15 and FIGS. 4-5 illustrate the increase in immune response of the primates administered with PIKA and PIKA Rabies Vaccine composition.

TABLE 14

Serum IgG (ELISA test)

| Days of Exam. | PIKA alone | PIKA Rabies composition (half) | PIKA Rabies composition (full) |
|---|---|---|---|
| Day 44 | 11,396 | 48,062 | 93,256 |
| Day 70 | 8,879 | 20,552 | 55,550 |

TABLE 15

Potency (FAVN test)

| Days of Exam. | PBS Control | PIKA | PIKA Rabies composition (half) | PIKA Rabies composition (full) |
|---|---|---|---|---|
| Day 44 | 0.115 | 0.113 | 4.795 | 7.366 |
| Day 70 | 0.115 | 0.890 | 5.653 | 5.670 |

On Day 44, PIKA rabies vaccine low and high dose groups induced on average 4.795 and 7.366 IU of neutralizing antibodies respectively in monkeys, i.e. 9.6 and 14.7 times more potent than the WHO required 0.5 IU protection level. The neutralizing antibody potency dropped slightly to 5.653 in high dose group and increased in low dose group to 5.670 on day 70.

In Summary, the rabies vaccine composition containing IPRV produced in Vero cell line are well tolerated and proved to have good immunogenicity in rhesus monkeys after repeated intramuscular injections over an observation period of 84 days. The specific antibodies are important in neutralizing the free virus and combating rabies viral infection.

The calculation of the margin of safety (MOS) is presented in Table 16 below and it is determined by: MOS=total primate dose tested (mg/kg)/proposed total human dose (mg/kg).

TABLE 16

Primate Chronic Toxicity - Margin of Safety

| Study Groups | Volume/ | | Effective Dose | |
|---|---|---|---|---|
| | Injection (regime) | Total volume/ Body weight | Total dose/ kg | MOS |
| Human Dose | 1.0 ml (2-2-1) | 5.0 ml/60 kgBW | 0.083 | / |
| Half-dose group | 0.5 ml (2-2-1-1-1) | 3.5 ml/3 kgBW | 1.667 | 14 |
| Full-dose group | 1.0 ml (2-2-1-1-1) | 7.0 ml/3 kgBW | 2.333 | 28 |

The margin of safety for the PIKA Rabies Vaccine when 2 IU IPRV and 1000 µg PIKA adjuvant with 0.3% HSA is used for human adult over the monkey toxicity test dosage is 28 fold for a full dose group and 14 fold for a half dose group.

Example 10. Safety and Efficacy Test in Healthy Volunteers

A phase I clinical trial with the rabies vaccine composition containing PIKA adjuvant (1 IU IPRV and 1000 µg PIKA adjuvant) is conducted. Healthy volunteers were divided into three groups with 10 subjects in each group. Subjects in each group were administered with the PIKA rabies vaccine composition or a comparator vaccine (9.4 IU IPRV) without adjuvant at days 0, 3, 7, 14 and 28. Blood samples were collected at days 0, 7, 10, 30 and 60 for neutralizing antibody titer evaluation with result showing below:

TABLE 17

| | The titer of neutralizing antibody (IU/ml) | |
|---|---|---|
| Days | Comparator vaccine | PIKA rabies vaccine |
| 0 | 0 | 0 |
| 7 | 0 | 0.13 |
| 10 | 0.25 | 0.42 |
| 30 | 3.24 | 5.32 |
| 60 | 8.55 | 17.81 |

Summary of findings: There was no obvious adverse effect observed during the trial. The rabies vaccine containing PIKA adjuvant was able to induce the neutralizing antibody as early as day 7 after the primary immunization. Comparing with the comparator vaccine, PIKA rabies vaccine produced earlier and higher-titer neutralizing antibody.

Example 11. Early Antibody Induction in Healthy Volunteers

In another pilot human trial evolving 4 healthy volunteers, subjects were administered with the rabies vaccine composition containing 2 IU IPRV and 1000 μg PIKA adjuvant using 2-2-1 regimen at days 0, 3 and 7 (i.e. 4 IU IPRV and 2000 μg PIKA adjuvant in total were administered at days 0 and 3 at two different sites). Blood samples were taken at days 0, 7 and 14 after immunization. Humoral immune response was evaluated with results tabulated in Table 18:

TABLE 18

| Average titer of neutralizing antibody (IU/ml) in 4 human subjects | | | |
|---|---|---|---|
| | Day 0 | Day 7 | Day 14 |
| Average antibody titer | 0.00 | 1.08 | 18.06 |

Summary of findings: The four volunteers did not report any obvious adverse effect during the trial. The rabies vaccine composition was able to induce the neutralizing antibody greater than 0.5 IU as early as day 7 after the primary immunization. This is considered protective according to WHO standard. Therefore, the vaccine dose up to 4 IU IPRV and 2000 μg PIKA adjuvant for first two injections is safe and effective in inducing early and high level of protective immunity in human subjects.

Example 12. Long Lasting Immune Response in Healthy Volunteers

Healthy volunteers were immunized with rabies vaccine containing 1.5 IU IPRV and 1,000 μg/ml PIKA adjuvant. Peripheral blood mononuclear cells were isolated from the blood samples collected 2.5 years after immunization. Cells were stimulated with PBS control or different level of IPRV and tested for Interferon-γ production using ELISPOT assay. The results showed that volunteers still produce significant level of Interferon-γ upon stimulation 2.5 years after immunizing with rabies vaccine containing PIKA adjuvant.

Example 13. Stability Analysis of the Freeze-Dried Rabies Vaccine

A long-term stability test at 2 to 8° C. and an accelerated test at 37° C. are planned to analyze the stability of the vaccine composition. Four batches of freeze-dried rabies vaccine composition (1.0 ml/vial) are tested (Batch No. II-20130401, II-20130402, II-20130501 and II-20130901).

The Compositions

Batch No. I1-20130402, the rabies vaccine composition comprises:
2.0 IU/dose IPRV, 1000 μg/dose PIKA adjuvant, 5.0% maltose, 0.3% HSA, and 7.60±0.05 PBS buffer.

Batch No. II-20130401, the rabies vaccine composition comprises:
1.5 IU/dose IPRV, 2000 μg/dose PIKA adjuvant, 5.0% maltose, 0.3% HSA, and 7.60±0.05 PBS buffer.

Batch No. II-20130501, the rabies vaccine composition comprises:
2.0 IU/dose IPRV, 2000 μg/dose PIKA adjuvant, 5.0% maltose, 0.3% HSA, and 7.60±0.05 PBS buffer.

Batch No. II-20130901, the rabies vaccine composition comprises:
4.0 IU/dose IPRV, 1000 μg/dose PIKA adjuvant, 5.0% maltose, 0.5% HSA, and 7.60±0.05 PBS buffer.

13.1. Long-Term Stability Test

The 4 batches of vaccine compositions above are stored at 2 to 8° C. for long-term stability test, which is planned out according to China and European pharmacopoeia standard over a period of 42 months. The items tested include appearance, pH, moisture content, endotoxin, sterility, potency, identification, residue bovine serum albumin, residue gentamycin sulfate, protein residue from host cell, Kanamycin content, PIKA content, PIKA molecular weight, and DNA residues from host cell.

The results up to 6 months are satisfactory according to China pharmacopoeia (2010 ed.) and European pharmacopoeia (E7.0) standard, the vaccine potency is still significantly higher than 2.5 IU/ml as WHO standard required. No significant deviation of the appearance, pH, moisture content, endotoxin, and sterility are observed from month 0.

13.2. Accelerated Stability Test

An accelerated stability test is also carried out on the above 3 batches by storing the vaccine at 37° C. for 6 months. It acted as a preliminary indication for long term stability. Quality tests for appearance, pH, moisture content, endotoxin, sterility, and vaccine potency are carried out at months 1, 2, 3, and 6 respectively. The test results for four batches of rabies vaccine composition described above are summarized in Table 19.

TABLE 19

| Results of accelerated stability test | | | | | | |
|---|---|---|---|---|---|---|
| | | | Test Items | | | |
| Storage Duration | Appearance | pH | Moisture content | Endotoxin | Sterility | Potency (IU) |
| Batch No. II-20130401 | | | | | | |
| 1 Month | Qualified | 7.4 | 1.6% | <25 | Qualified | 6.6 |
| 2 Months | Qualified | 7.4 | 1.6% | <25 | Qualified | 9.1 |
| 3 Months | Qualified | 7.4 | 1.6% | <25 | Qualified | 6.2 |
| 6 Months | Qualified | 7.5 | 1.6% | <25 | Qualified | 8.1 |
| Batch No. II-20130402 | | | | | | |
| 1 Month | Qualified | 7.4 | 1.5% | <25 | Qualified | 4.9 |
| 2 Months | Qualified | 7.4 | 1.5% | <25 | Qualified | 9.5 |
| 3 Months | Qualified | 7.4 | 1.7% | <25 | Qualified | 5.5 |
| 6 Months | Qualified | 7.4 | 1.7% | <25 | Qualified | 8.1 |
| Batch No. II-20130501 | | | | | | |
| 1 Month | Qualified | 7.4 | 1.6% | <25 | Qualified | 5.7 |
| 2 Months | Qualified | 7.4 | 1.6% | <25 | Qualified | 10.0 |
| 3 Months | Qualified | 7.4 | 1.6% | <25 | Qualified | 6.2 |

TABLE 19-continued

Results of accelerated stability test

| Storage Duration | Appearance | pH | Moisture content | Endotoxin | Sterility | Potency (IU) |
|---|---|---|---|---|---|---|
| 6 Months | Qualified | 7.4 | 1.6% | <25 | Qualified | 9.1 |
| | | | Batch No. II-20130901 | | | |
| 1 Month | Qualified | 7.5 | 1.1% | <25 | Qualified | 7.4 |
| 2 Months | Qualified | 7.6 | 1.1% | <25 | Qualified | 11.7 |
| 3 Months | Qualified | 7.6 | 1.2% | <25 | Qualified | 7.2 |
| 6 Months | — | — | — | — | — | — |

After storing at 37° C. for 1, 2, 3, and 6 month(s), the vaccine is still significantly higher than 2.5 IU/ml which is the standard requirement of WHO. No significant deviation of the appearance, pH, moisture content, endotoxin, and sterility are observed from month 0. The results act as a preliminary indication for long term stability of the rabies vaccine composition.

The invention claimed is:

1. A rabies vaccine composition, comprising:
 a) inactivated purified rabies virus (IPRV),
 b) PIKA adjuvant, and
 c) human serum albumin (HSA);
 wherein
 the amount of IPRV is from 0.5 IU to 3.0 IU per unit dose,
 the amount of PIKA adjuvant is from 250 µg to 3000 µg per unit dose, and
 the amount of HSA is from 0.1% to 0.9% by concentration.

2. The rabies vaccine composition according to claim 1, wherein the amount of said IPRV is selected from the group consisting of 0.5 IU, 1.0 IU, 1.5 IU, 2.0 IU, 2.5 IU, and 3.0 IU per unit dose, and the range between any two of the following amounts: 0.5 IU, 1.0 IU, 1.5 IU, 2.0 IU, 2.5 IU, and 3.0 IU per unit dose.

3. The rabies vaccine composition according to claim 2, wherein the amount of said IPRV is from 0.5 IU to 3.0 IU per unit dose or from 1.0 IU to 2.5 IU per unit dose.

4. The rabies vaccine composition according to claim 1, wherein the amount of said PIKA adjuvant is selected from the group consisting of 250 µg, 500 µg, 1000 µg, 1500 µg, 2000 µg, and 3000 µg per unit dose, and the range between any two of the following amounts: 250 µg, 500 µg, 1000 µg, 1500 µg, 2000 µg, and 3000 µg per unit dose.

5. The rabies vaccine composition according to claim 4, wherein the amount of said PIKA adjuvant is between from 500 µg to 3000 µg per unit dose, or from 1000 µg to 3000 µg, or from 1500 µg to 2500 µg, or about 2000 µg per unit dose.

6. The rabies vaccine composition according to claim 1, wherein the amount of said HSA is selected from the group consisting of 0.2%, 0.25%, 0.3%, 0.35%, 0.4%, 0.45%, 0.5%, and 0.6% by concentration, and the range between any two of the following amounts: 0.2%, 0.25%, 0.3%, 0.35%, 0.4%, 0.45%, 0.5%, and 0.6% by concentration.

7. The rabies vaccine composition according to claim 1, wherein the ratio of IPRV to PIKA adjuvant is selected from the group consisting of: 1 IU/100 µg, 1 IU/125 µg, 1 IU/200 µg, 1 IU/250 µg, 1 IU/300 µg, 1 IU/350 µg, 1 IU/400 µg, 1 IU/450 µg, 1 IU/500 µg, 1 IU/550 µg, 1 IU/600 µg, 1 IU/700 µg, 1 IU/800 µg, 1 IU/1000 µg, 1 IU/1500 µg, and 1 IU/2000 µg, and the ratio between any two of the following ratios: 1 IU/100 µg, 1 IU/125 µg, 1 IU/200 µg, 1 IU/250 µg, 1 IU/300 µg, 1 IU/350 µg, 1 IU/400 µg, 1 IU/450 µg, 1 IU/500 µg, 1 IU/550 µg, 1 IU/600 µg, 1 IU/700 µg, 1 IU/800 µg, 1 IU/1000 µg, 1 IU/1500 µg, and 1 IU/2000 µg.

8. The rabies vaccine composition according to claim 1, wherein the amount of IPRV is 2.0 IU per unit dose, and the amount of PIKA adjuvant is 1000 µg per unit dose.

9. The rabies vaccine composition according to claim 1, wherein the amount of IPRV is 2.0 IU per unit dose, the amount of PIKA adjuvant is 2000 µg per unit dose, and the amount of HSA is 0.3% by concentration.

10. The rabies vaccine composition according to claim 1, wherein the amount of IPRV is 1.5 IU per unit dose, the amount of PIKA adjuvant is 2000 µg per unit dose, and the amount of HSA is 0.3% by concentration.

11. The rabies vaccine composition according to claim 1, wherein the amount of IPRV is 2.0 IU per unit dose, the amount of PIKA adjuvant is 1000 µg per unit dose, and the amount of HSA is 0.5% by concentration.

12. The rabies vaccine composition according to claim 1, wherein said composition does not comprise gelatin.

13. The rabies vaccine composition according to claim 1, wherein said composition further comprises maltose, wherein the amount of said maltose is between 1.0% and 6.0% by concentration.

14. The rabies vaccine composition according to claim 1, wherein said IPRV is selected from the group consisting of CTN strain, PM strain, aG strain, and PV strain.

15. The rabies vaccine composition according to claim 1, wherein said IPRV is prepared in Vero cell or primary hamster kidney cell.

16. The rabies vaccine composition according to claim 1, wherein said composition is in a liquid form or a lyophilized form.

17. A pharmaceutical kit, comprising or consisting of:
 a) the rabies vaccine composition of claim 1,
 b) a vial,
 c) an instruction for use, and
 d) optionally water for injection;
 wherein said instruction for use suggests the following administration regimen:
  1) 2-2-1 regimen for post exposure treatment: 2 unit dose administered on days 0, 2 unit dose administered on days 3, and 1 unit dose administered on days 7 post exposure; and/or
  2) 2-1 regimen for prophylaxis: 2 unit dose administered on days 0 and 1 unit dose administered on days 7.

18. A method for treatment or prevention of rabies caused by rabies virus infection or inducing an immune response to rabies virus infection, wherein the method comprises a step of administering the rabies vaccine composition of claim 1 to a host, wherein said host has been exposed to rabies virus.

19. The method according to claim 18, wherein the rabies vaccine composition of claim 1 is administered to the host for 5 times within 7 days post exposure of rabies virus.

20. The method according to claim 19, wherein the rabies vaccine composition of claim 1 is administered to the host based on the following regimen:
 a first administration on 0 day post exposure,
 a second administration on 0 day post exposure,
 a third administration on 2 or 3 day post exposure,
 a fourth administration on 2 or 3 day post exposure, and
 a fifth administration on 6 or 7 day post exposure, respectively.

21. The method according to claim 18, wherein the rabies vaccine composition of claim 1 is administered to a host based on the following regimen:
 a 1st and a 2nd administration on 0 day post exposure, a 3rd and a 4th administration on 2 or 3 day post exposure, and a 5th and/or a 6th administration on 7 day post exposure, respectively.

22. A method for prophylaxis of rabies caused by rabies virus infection or inducing an immune response to a rabies virus, the method comprises a step of administering the rabies vaccine composition of claim 1 to a host, wherein said host is not exposed to rabies virus.

23. The method according to claim 22, wherein the rabies vaccine composition of claim 1 is administered to the host for 3 times within 7 days.

24. The method according to claim 23, wherein the rabies vaccine composition of claim 1 is administered to the host based on the following regimen:

a first administration on day 0, a second administration on day 0, and a third administration on day 7, respectively.

25. The method according to claim 18, wherein said administration is by intramuscular injection, intradermal delivery, transdermal delivery, subcutaneous injection, parenteral injection, intraperitoneal injection, intravenous injection, inhalation, rectal delivery, nasal delivery, oral delivery, or topical delivery.

26. A method of medical treatment, wherein the method involves administering the rabies vaccine composition according to claim 1 five or six times within seven days.

27. The method according to claim 26, wherein the method involves administering the rabies vaccine composition based on the following regimen:

a 1st and a 2nd administration on 0 day post exposure, a 3rd and a 4th administration on 2 or 3 day post exposure, and a 5th and/or a 6th administration on 7 day post exposure, respectively.

28. A method of prevention of rabies, wherein the method involves administering the rabies vaccine composition according to claim 1 three times within seven days.

29. The method according to claim 28, wherein the method of prevention involves administering the rabies vaccine composition based on the following regimen:

a first administration on day 0, a second administration on day 0, and a third administration on day 7, respectively.

* * * * *

UNITED STATES PATENT AND TRADEMARK OFFICE
CERTIFICATE OF CORRECTION

PATENT NO. : 12,097,254 B2
APPLICATION NO. : 17/211632
DATED : September 24, 2024
INVENTOR(S) : Li et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this
Third Day of December, 2024

Katherine Kelly Vidal
*Director of the United States Patent and Trademark Office*